US009023074B2

(12) United States Patent
Theobald et al.

(10) Patent No.: US 9,023,074 B2
(45) Date of Patent: May 5, 2015

(54) MULTI-STAGE OCCLUSION DEVICES

(75) Inventors: Elizabeth Theobald, Bloomington, IN (US); James R. Randolph, Bloomington, IN (US); Dusan Pavcnik, Portland, OR (US); Frederick Keller, Portland, OR (US); Brad Shirley, Bloomington, IN (US); Sean Chambers, Bloomington, IN (US); Ram Paul, Bloomington, IN (US); Rodney Thurman, Bloomington, IN (US); Michael Deckard, Solsberry, IN (US)

(73) Assignees: Cook Medical Technologies LLC, Bloomington, IN (US); Oregon Health and Science University, Portland, OR (US)

( * ) Notice: Subject to any disclaimer, the term of this patent is extended or adjusted under 35 U.S.C. 154(b) by 343 days.

(21) Appl. No.: 13/461,260

(22) Filed: May 1, 2012

(65) Prior Publication Data

US 2013/0116720 A1 May 9, 2013

Related U.S. Application Data

(63) Continuation-in-part of application No. PCT/US2011/056278, filed on Oct. 14, 2011.

(60) Provisional application No. 61/393,624, filed on Oct. 15, 2010, provisional application No. 61/498,048, filed on Jun. 17, 2011.

(51) Int. Cl.
*A61M 29/00* (2006.01)
*A61B 17/12* (2006.01)
*A61B 17/00* (2006.01)

(52) U.S. Cl.
CPC ......... *A61B 17/1214* (2013.01); *A61B 17/0057* (2013.01); *A61B 2017/00597* (2013.01)

(58) Field of Classification Search
CPC .............. A61B 17/0057; A61B 2017/00597; A61B 2017/00575; A61B 2017/00592; A61B 2017/00606; A61B 17/1214; A61F 2/2418; A61F 2/2475
USPC ......... 606/157, 159, 191, 194, 198, 200, 213; 623/1.11, 1.24, 2.11, 2.13
See application file for complete search history.

(56) References Cited

U.S. PATENT DOCUMENTS

| 3,012,882 | A | 12/1961 | Muldawer et al. |
| 3,174,851 | A | 3/1965 | Buehler et al. |

(Continued)

FOREIGN PATENT DOCUMENTS

| EP | 1281355 | 2/2003 |
| JP | 02-307480 | 12/1990 |

(Continued)

OTHER PUBLICATIONS

European Patent Office, European Search Report & Written Opinion of the International Searching Authority, Apr. 18, 2012, for International Application No. PCT/US2011/056278.

(Continued)

*Primary Examiner* — Katherine M Shi
(74) *Attorney, Agent, or Firm* — Buchanan Nipper

(57) ABSTRACT

An occlusion device has a covering attached to a support frame that includes a disc-shaped member and a crossbar that extends across a central opening defined by the disc-shaped member. The occlusion device has a first, or deployed, configuration in which the crossbar defines a curve that extends from the disc-shaped member, and a second, or resting, configuration in which the disc-shaped member and the crossbar lie substantially in a single plane. Each of the disc-shaped member and the crossbar include a core wire that extends through a lumen of a coil multiple times.

13 Claims, 12 Drawing Sheets

(56) References Cited

U.S. PATENT DOCUMENTS

| | | |
|---|---|---|
| 3,772,137 A | 11/1973 | Tolliver |
| 3,953,566 A | 4/1976 | Gore |
| 4,665,906 A | 5/1987 | Jervis |
| 4,675,361 A | 6/1987 | Ward, Jr. |
| 4,836,204 A | 6/1989 | Landymore et al. |
| 4,861,830 A | 8/1989 | Ward, Jr. |
| 4,911,163 A | 3/1990 | Fina |
| 4,917,089 A | 4/1990 | Sideris |
| 5,017,664 A | 5/1991 | Grasel et al. |
| 5,020,612 A | 6/1991 | Williams |
| 5,024,671 A | 6/1991 | Tu et al. |
| 5,108,420 A | 4/1992 | Marks |
| 5,167,628 A | 12/1992 | Boyles |
| 5,176,692 A | 1/1993 | Wilk et al. |
| 5,192,301 A | 3/1993 | Kamiya et al. |
| 5,258,000 A | 11/1993 | Gianturco |
| 5,284,488 A | 2/1994 | Sideris |
| 5,334,217 A | 8/1994 | Das |
| 5,417,708 A | 5/1995 | Hall et al. |
| 5,425,744 A | 6/1995 | Fagan et al. |
| 5,433,727 A | 7/1995 | Sideris |
| 5,451,235 A | 9/1995 | Lock et al. |
| 5,486,195 A | 1/1996 | Myers et al. |
| 5,589,563 A | 12/1996 | Ward et al. |
| 5,595,571 A | 1/1997 | Jaffe et al. |
| 5,634,936 A | 6/1997 | Linden et al. |
| 5,643,317 A | 7/1997 | Pavcnik et al. |
| 5,669,933 A | 9/1997 | Simon et al. |
| 5,683,411 A | 11/1997 | Kavteladze et al. |
| 5,690,642 A | 11/1997 | Osborne et al. |
| 5,702,421 A | 12/1997 | Schneidt |
| 5,709,707 A | 1/1998 | Lock et al. |
| 5,720,777 A | 2/1998 | Jaffe |
| 5,725,534 A | 3/1998 | Rasmussen |
| 5,733,337 A | 3/1998 | Carr, Jr. et al. |
| 5,769,796 A | 6/1998 | Palermo et al. |
| 5,772,632 A | 6/1998 | Forman |
| 5,797,953 A | 8/1998 | Tekulve |
| 5,797,960 A | 8/1998 | Stevens et al. |
| 5,814,061 A | 9/1998 | Osborne et al. |
| 5,843,180 A | 12/1998 | Jaffe et al. |
| 5,843,181 A | 12/1998 | Jaffe et al. |
| 5,846,247 A | 12/1998 | Unsworth et al. |
| 5,846,261 A | 12/1998 | Kotula et al. |
| 5,853,422 A | 12/1998 | Huebsch et al. |
| 5,861,003 A | 1/1999 | Latson et al. |
| 5,879,366 A | 3/1999 | Shaw et al. |
| 5,944,738 A | 8/1999 | Amplatz et al. |
| 5,947,997 A | 9/1999 | Pavcnik et al. |
| 5,960,642 A | 10/1999 | Kim et al. |
| 5,976,174 A | 11/1999 | Ruiz |
| 5,980,799 A | 11/1999 | Martakos et al. |
| 5,993,844 A | 11/1999 | Abraham et al. |
| 6,063,113 A | 5/2000 | Kavteladze et al. |
| 6,077,281 A | 6/2000 | Das |
| 6,077,291 A | 6/2000 | Das |
| 6,080,182 A | 6/2000 | Shaw et al. |
| 6,113,623 A | 9/2000 | Sgro |
| 6,117,157 A | 9/2000 | Tekulve |
| 6,117,159 A | 9/2000 | Huebsch et al. |
| 6,174,322 B1 | 1/2001 | Schneidt |
| 6,193,731 B1 | 2/2001 | Oppelt |
| 6,206,907 B1 | 3/2001 | Marino et al. |
| 6,206,931 B1 | 3/2001 | Cook et al. |
| 6,214,029 B1 | 4/2001 | Thill et al. |
| 6,238,416 B1 | 5/2001 | Sideris |
| 6,264,677 B1 | 7/2001 | Simon et al. |
| 6,296,657 B1 | 10/2001 | Brucker |
| 6,346,074 B1 | 2/2002 | Roth |
| 6,355,052 B1 | 3/2002 | Neuss et al. |
| 6,358,228 B1 | 3/2002 | Tubman et al. |
| 6,358,284 B1 | 3/2002 | Fearnot et al. |
| 6,368,338 B1 | 4/2002 | Konya et al. |
| 6,371,961 B1 | 4/2002 | Osborne et al. |
| 6,379,368 B1 | 4/2002 | Corcoran et al. |
| 6,451,052 B1 | 9/2002 | Burmeister et al. |
| 6,458,137 B1 | 10/2002 | Klint |
| 6,547,815 B2 | 4/2003 | Myers et al. |
| 6,572,650 B1 | 6/2003 | Abraham et al. |
| 6,623,508 B2 | 9/2003 | Shaw et al. |
| 6,656,206 B2 | 12/2003 | Corcoran et al. |
| 6,673,100 B2 | 1/2004 | Diaz et al. |
| 6,692,458 B2 | 2/2004 | Forman et al. |
| 6,723,108 B1 | 4/2004 | Jones et al. |
| 6,749,622 B2 | 6/2004 | McGuckin, Jr. et al. |
| 6,752,826 B2 | 6/2004 | Holloway et al. |
| 6,783,499 B2 | 8/2004 | Schwartz |
| 6,790,218 B2 | 9/2004 | Jayaraman |
| 6,911,037 B2 | 6/2005 | Gainor et al. |
| 6,939,377 B2 | 9/2005 | Jayaraman et al. |
| 6,949,113 B2 | 9/2005 | Van Tassel et al. |
| 6,949,116 B2 | 9/2005 | Solymar et al. |
| 6,960,220 B2 | 11/2005 | Marino et al. |
| 6,974,474 B2 | 12/2005 | Pavcnik et al. |
| 6,994,092 B2 | 2/2006 | Van der Berg et al. |
| 6,994,717 B2 | 2/2006 | Konya et al. |
| 7,101,381 B2 | 9/2006 | Ford et al. |
| 7,101,395 B2 | 9/2006 | Tremulis et al. |
| 7,128,073 B1 | 10/2006 | Van der Burg |
| 7,144,410 B2 | 12/2006 | Marino et al. |
| 7,288,105 B2 | 10/2007 | Oman et al. |
| 7,658,751 B2 | 2/2010 | Stone et al. |
| 8,366,741 B2 | 2/2013 | Chin et al. |
| 8,366,743 B2 | 2/2013 | Zeng |
| 8,480,707 B2 | 7/2013 | Pavcnik et al. |
| 8,617,205 B2 | 12/2013 | Pavcnik et al. |
| 8,702,746 B2 | 4/2014 | Tekulve et al. |
| 2001/0034537 A1 | 10/2001 | Shaw et al. |
| 2001/0037129 A1 | 11/2001 | Thill |
| 2001/0039450 A1 | 11/2001 | Pavcnik et al. |
| 2002/0111647 A1 | 8/2002 | Khairkhahan et al. |
| 2002/0169475 A1 | 11/2002 | Gainor et al. |
| 2002/0183787 A1 | 12/2002 | Wahr et al. |
| 2002/0187288 A1 | 12/2002 | Lim et al. |
| 2002/0198563 A1 | 12/2002 | Gainor et al. |
| 2003/0028213 A1 | 2/2003 | Thill et al. |
| 2003/0065361 A1 | 4/2003 | Dreyfuss |
| 2003/0093108 A1 | 5/2003 | Avellanet et al. |
| 2003/0130713 A1 | 7/2003 | Stewart et al. |
| 2003/0139819 A1 | 7/2003 | Beer et al. |
| 2003/0144694 A1 | 7/2003 | Chanduszko et al. |
| 2003/0149471 A1 | 8/2003 | Briana et al. |
| 2003/0191495 A1 | 10/2003 | Ryan et al. |
| 2003/0206860 A1 | 11/2003 | Bleyer et al. |
| 2004/0073242 A1 | 4/2004 | Chanduszko |
| 2004/0078053 A1 | 4/2004 | Berg et al. |
| 2004/0093017 A1 | 5/2004 | Chanduszko |
| 2004/0098030 A1 | 5/2004 | Makower et al. |
| 2004/0098042 A1 | 5/2004 | Devellian et al. |
| 2004/0133236 A1 | 7/2004 | Chanduszko et al. |
| 2004/0143277 A1 | 7/2004 | Marino et al. |
| 2004/0143291 A1 | 7/2004 | Corcoran et al. |
| 2004/0143292 A1 | 7/2004 | Marino et al. |
| 2004/0143293 A1 | 7/2004 | Marino et al. |
| 2004/0143294 A1 | 7/2004 | Corcoran et al. |
| 2004/0166169 A1 | 8/2004 | Malaviya et al. |
| 2004/0176799 A1 | 9/2004 | Chanduszko et al. |
| 2004/0213756 A1 | 10/2004 | Michal et al. |
| 2004/0220596 A1 | 11/2004 | Frazier et al. |
| 2004/0220610 A1 | 11/2004 | Kreidler et al. |
| 2004/0230222 A1 | 11/2004 | Van der Burg et al. |
| 2004/0260340 A1 | 12/2004 | Jacobs et al. |
| 2004/0267191 A1 | 12/2004 | Gifford, III et al. |
| 2004/0267306 A1 | 12/2004 | Blaeser et al. |
| 2005/0010248 A1 | 1/2005 | Lafontaine |
| 2005/0034735 A1 | 2/2005 | Deem et al. |
| 2005/0043759 A1 | 2/2005 | Chanduszko |
| 2005/0049634 A1 | 3/2005 | Chopra |
| 2005/0065547 A1 | 3/2005 | Marino et al. |
| 2005/0065548 A1 | 3/2005 | Marino et al. |
| 2005/0070794 A1 | 3/2005 | Deal et al. |
| 2005/0070821 A1 | 3/2005 | Deal et al. |
| 2005/0085843 A1 | 4/2005 | Opolski et al. |
| 2005/0125032 A1 | 6/2005 | Whisenant et al. |

(56) References Cited

U.S. PATENT DOCUMENTS

| | | |
|---|---|---|
| 2005/0125050 A1 | 6/2005 | Carter et al. |
| 2005/0192626 A1 | 9/2005 | Widomski et al. |
| 2005/0192627 A1 | 9/2005 | Whisenant et al. |
| 2005/0203568 A1 | 9/2005 | Burg et al. |
| 2005/0228434 A1 | 10/2005 | Amplatz et al. |
| 2005/0234509 A1 | 10/2005 | Widomski et al. |
| 2005/0249772 A1 | 11/2005 | Malaviya et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267524 A1 | 12/2005 | Chanduszko |
| 2005/0267526 A1 | 12/2005 | Wahr et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0283187 A1 | 12/2005 | Longson |
| 2005/0288682 A1 | 12/2005 | Howe |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0036282 A1 | 2/2006 | Wahr et al. |
| 2006/0052816 A1 | 3/2006 | Bates et al. |
| 2006/0052821 A1 | 3/2006 | Abbott et al. |
| 2006/0106418 A1 | 5/2006 | Seibold et al. |
| 2006/0106420 A1 | 5/2006 | Dolan et al. |
| 2006/0122646 A1 | 6/2006 | Corcoran et al. |
| 2006/0122647 A1 | 6/2006 | Callaghan et al. |
| 2006/0155327 A1 | 7/2006 | Briganti et al. |
| 2006/0200196 A1 | 9/2006 | Zang et al. |
| 2006/0201996 A1 | 9/2006 | Hodde |
| 2006/0210603 A1 | 9/2006 | Williams et al. |
| 2006/0216326 A1 | 9/2006 | Pacetti |
| 2006/0217760 A1 | 9/2006 | Widomski et al. |
| 2006/0217761 A1 | 9/2006 | Opolski |
| 2006/0229670 A1 | 10/2006 | Bates |
| 2006/0235467 A1 | 10/2006 | DeVore |
| 2006/0241687 A1 | 10/2006 | Glaser et al. |
| 2006/0271030 A1 | 11/2006 | Francis et al. |
| 2008/0091235 A1 | 4/2008 | Sirota |
| 2009/0062836 A1 | 3/2009 | Kurrus |
| 2009/0062844 A1 | 3/2009 | Tekulve |
| 2010/0030246 A1 | 2/2010 | Pavcnik et al. |
| 2010/0030259 A1 | 2/2010 | Pavcnik et al. |
| 2010/0312272 A1 | 12/2010 | Pavcnik et al. |
| 2013/0116720 A1 | 5/2013 | Theobald et al. |

FOREIGN PATENT DOCUMENTS

| | | |
|---|---|---|
| WO | WO9310714 | 6/1993 |
| WO | WO9407560 | 4/1994 |
| WO | WO9527448 | 10/1995 |
| WO | WO9728744 | 8/1997 |
| WO | WO9827868 | 7/1998 |
| WO | WO2005020612 | 3/2005 |
| WO | WO2005027752 | 3/2005 |
| WO | WO2006110147 | 10/2006 |
| WO | WO2007092274 | 8/2007 |
| WO | 2008094706 | 8/2008 |
| WO | WO2008094691 | 8/2008 |
| WO | WO2012051489 | 4/2012 |

OTHER PUBLICATIONS

Braun, M., et al., "Transcatheter Closure of Patent Foramen Ovale (PFO) in Patients With Paradoxical Embolism", European Heart Journal (2004), vol. 25, pp. 424-430.

Das, Gladwin S., et al., "Experimental Atrial Septal Defect Closure With a New, Transcatheter, Self-Centering Device", Circulation, vol. 88, No. 4, Part 1, Oct. 1993, pp. 1754-1764.

Heeschen, Christopher, et al., "Nicotine Stimulates Angiogensis and Promotes Tumor Growth and Atherosclerosis", Nature Medicine vol. 7, No. 7, (Jul. 2001), pp. 833-839.

Johnson, Chad, et al., "Matrix Metalloproteinase-9 is Required for Adequate Angiogenic Revascularization of Ischemic Tissues", Circulation Research, Feb. 6, 2004, No. 94, pp. 262-268.

Jux, Christian, et al., "A New Biological Matrix for Septal Occlusion", Journal of Interventional Cardiology, vol. 16, No. 2, (2003), pp. 149-152.

King, Terry D., et al., "Secundum Atrial Septal Defect-Nonoperative Closure During Cardiac Catheterization", JAMA, vol. 235, No. 23, Jun. 7, 1978, pp. 2506-2509.

Mullen, Michael J., et al., "BioSTAR Evaluation STudy (BEST) A Prospective, Multicenter, Phase I Clinic Trial to Evaluate the Feasibility, Efficacy, and Safety of the BioSTAR Bioabsorbable Septal Repair Implant for the Closure of Atrial-Level Shunts", Circulation, Oct. 31, 2006, pp. 19621967.

Oguchi, M., et al., "Mucosa-adhesive water-soluble polymer film for treatment of acute radiation-induced oral mucositis", International Journal of Radiation Oncology Biology Physics, Mar. 15, 1998, vol. 40, No. 5, p. 1033-1037.

Pavcnik, Dusan et al., "Monodisk: Device for Percutaneous Transcatheter Closure of Cardiac Septal Defects", Cardiovasc Intervent Radio (1993) vol. 16, pp. 308-312.

Rashkind, William J., "Transcatheter Treatment of Congenital Heart Disease", Circulation vol. 67, No. 4, Apr. 1983, pp. 711-716.

Sideris, E.B. et al., "Transvenous Atrial Septal Defect Occlusion in Piglets with a 'Buttoned' Double-Disk Device", Circulation, vol. 81, No. 1, Jan. 1990, pp. 312-318.

Jux, Christian, et al., "Interventional Atrial Septal Defect Closure Using a Totally Bioresorbable Occluder Matrix", JACC, vol. 48, No. 1 (2006), pp. 161-169.

Babic, Uros U., et al., "Transcatheter Closure of Atrial Septal Defects", The Lancet, Sep. 1, 1990, pp. 566-567.

Bhattathiri, VN, et al., "Influence of plasma GSH level on acute radiation mucositis of the oral cavity", International Journal of Radiation Oncology Biology Physics (1994), vol. 29, No. 2, pp. 383-386.

Complete Prosecution History, U.S. Appl. No. 13/461,260, Compiled Feb. 13, 2014.

International Preliminary Report on Patentability for International Application No. PCT/2011/056278, Apr. 25, 2013, p. 1-8.

Kushwaha et al., A Nitric Oxide Releasing, Self Assembled Peptide Amphiphile Matrix That Mimics Native Endothelium for Coating Implantable Cardiovascular Devices, BioMaterials vol. 31, Issue 7 (2010) p. 1502-1508.

Taite et al., Nitric Oxide-Releasing Polyurethane-PEF Copolymer Containing the YIGSR Peptide Promotes Endothelialization With Decreased Platelet Adhesion, Journal of Biomedical Materials Research Part B: Applied Biomaterials, vol. 84B, Issue 1, (Jan. 2008) pp. 108-116.

Office Action Summary for U.S. Appl. No. 12/533,738, Issued by the USPTO, Sep. 22, 2011, pp. 1-9.

Office Action Summary for U.S. Appl. No. 12/533,738, Issued by the USPTO, Feb. 1, 2012, pp. 1-10.

Office Action Summary for U.S. Appl. No. 12/533,738, Issued by the USPTO, Jun. 6, 2012, pp. 1-13.

Office Action Summary for U.S. Appl. No. 12/533,738, Issued by the USPTO, Jan. 18, 2013, pp. 1-9.

U.S. Appl. No. 12/533,738, Dusan Pavcnik, Closure Device and Method for Occluding a Bodily Passage, filed Jul. 31, 2009; Notice of Allowance mailed Mar. 25, 2013.

Written Opinion of the International Searching Authority for International Application No. PCT/US2008/001376, Aug. 1, 2009, p. 1-8.

International Preliminary Report on Patentability for International Application No. PCT/US2008/001376, Aug. 4, 2009.

International Search Report for International Application No. PCT/US2008/094691, Jan. 5, 2009, p. 1-7.

Office Action Summary for U.S. Appl. No. 12/533,731, Issued by the USPTO, Sep. 6, 2012, pp. 1-12.

Written Opinion of the International Searching Authority for International Application No. PCT/US2008/001422, Aug. 1, 2009, p. 1-13.

International Preliminary Report on Patentability for International Application No. PCT/US2008/001422, Aug. 4, 2009.

(56) References Cited

OTHER PUBLICATIONS

International Search Report for International Application No. PCT/US2008/001422, Jan. 5, 2009, p. 1-8.

Office Action Summary for U.S. Appl. No. 12/813,489, Issued by the USPTO, Sep. 10, 2012, pp. 1-11.

U.S. Appl. No. 12/813,489, Dusan Pavcnik, Closure Device, filed Jun. 10, 2010; Notice of Allowance mailed Aug. 9, 2013.

Office Action Summary for U.S. Appl. No. 12/533,731, Issued by the USPTO, Aug. 16, 2013, pp. 1-12.

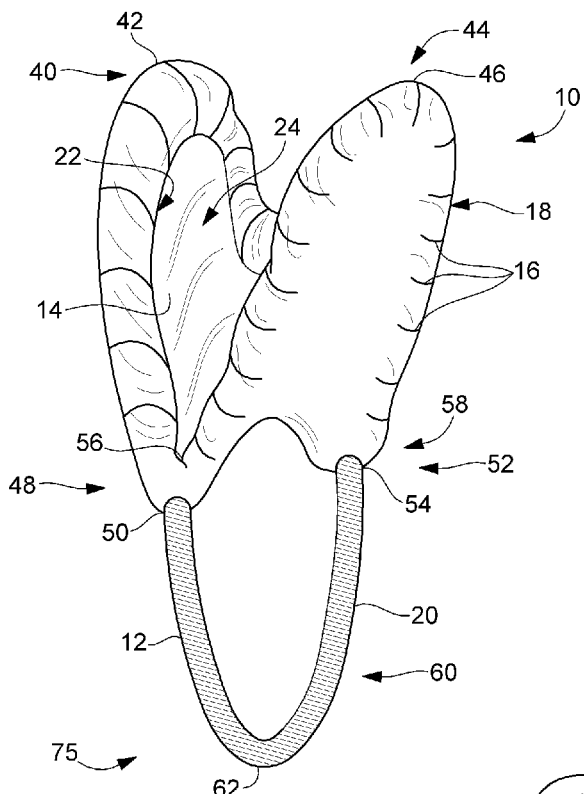
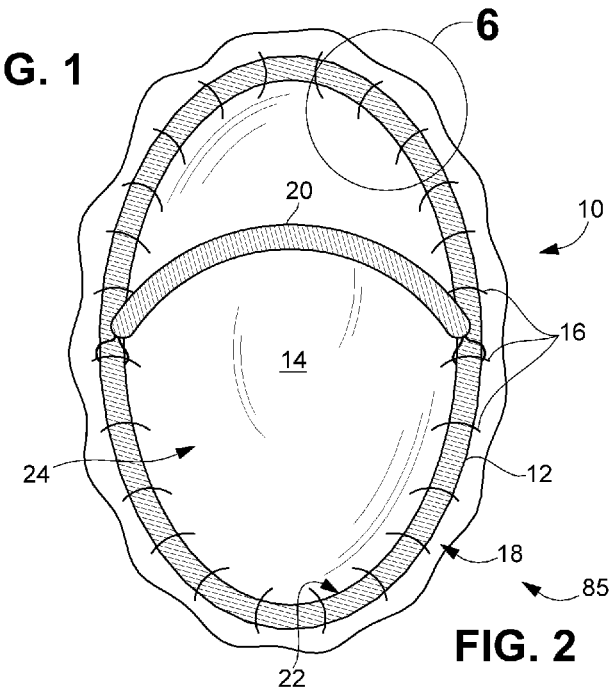

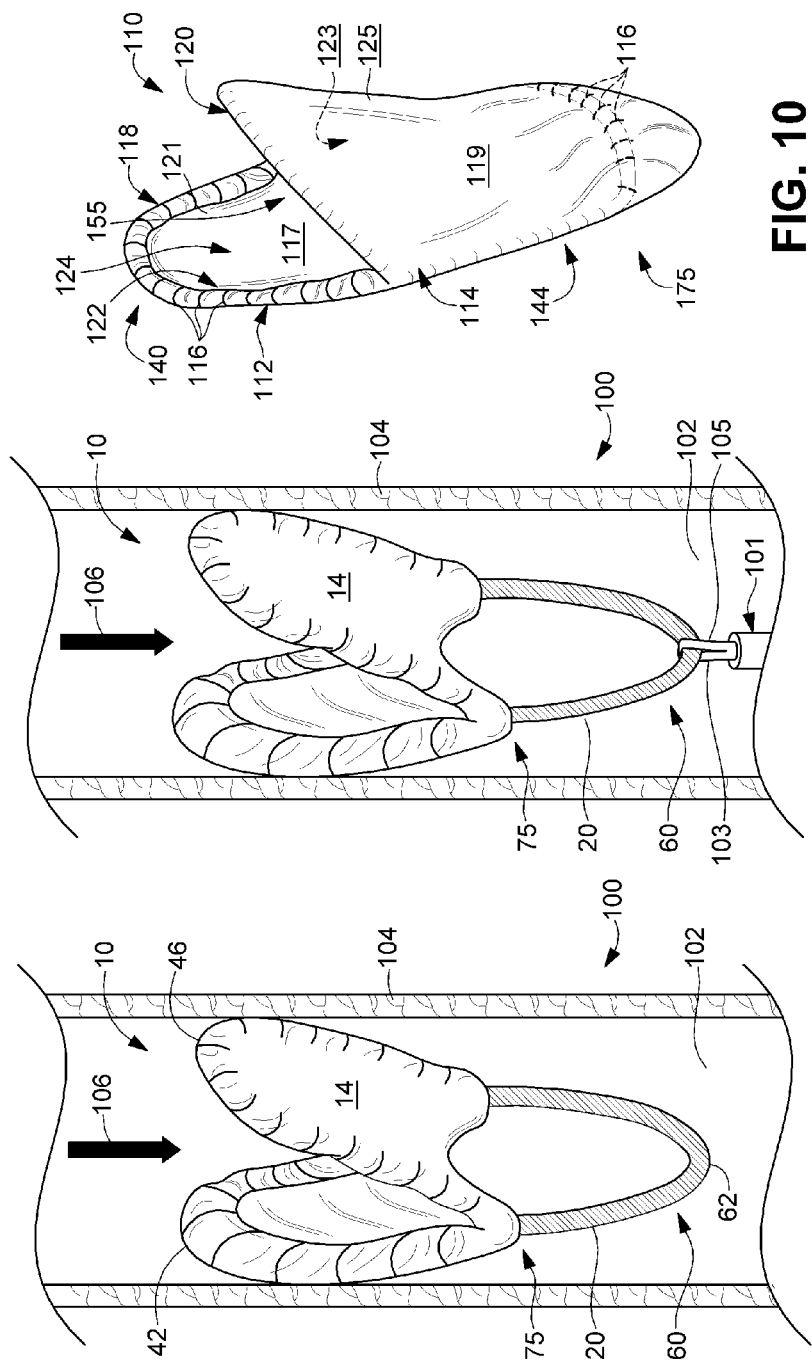

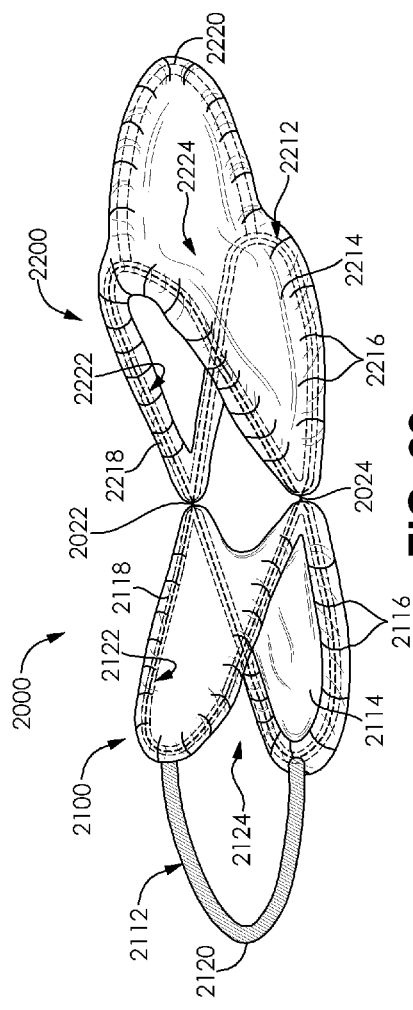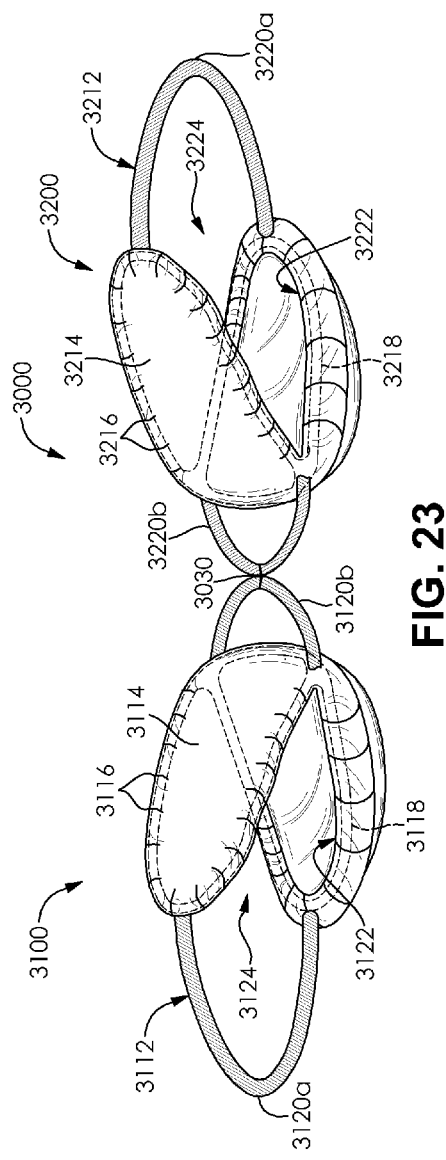

MULTI-STAGE OCCLUSION DEVICES

CROSS-REFERENCE TO RELATED APPLICATIONS

This application is a continuation-in-part application of International Patent Application Serial No. PCT/US2011/056278, filed on Oct. 14, 2011, which claims priority to U.S. Provisional Application Ser. No. 61/393,624, filed on Oct. 15, 2010, and U.S. Provisional Application Ser. No. 61/498,048, filed on Jun. 17, 2011. Each of these applications is hereby incorporated by reference into this disclosure in its entirety.

FIELD

The disclosure relates generally to the field of intraluminal medical devices. More particularly, the disclosure relates to occlusion devices for placement in bodily passages. The devices described herein are useful in the temporary or permanent blockage of fluid flow through various types of bodily passages, such as arteries, veins, fistulas, and other passages.

BACKGROUND

Intraluminal occlusion devices are used to block fluid flow through bodily passages. In certain clinical situations, such as surgical procedures during which a bloodless field is desired, a temporary blockage of fluid flow is desired. In other situations, a permanent blockage of fluid flow is desired.

The art contains a variety of occlusion devices that perform the occlusion function with various degrees of efficiency and effectiveness. Several of these devices, however, have drawbacks that limit their usability. For example, some occlusion devices, such as the Amplatzer Septal Occluder (AGA Medical Corporation, Plymouth, Minn.), contain complex, multi-filament frame structures that contribute significant bulk to the overall profile of the occlusion device, effectively limiting its use to only relatively large bodily passages that can accommodate the bulk of the device and the catheter used to deliver and deploy the device. Also, many occlusion devices rely on thrombosis—the formation of a thrombus at the site of deployment of the occlusion device—as the mechanism for occlusion. While such devices may provide the desired blockage once a thrombus forms, the thrombus can be partially reabsorbed over time, which may reduce the effectiveness of these occlusion devices as the embolized bodily passage becomes recanalized and fluid flow is restored. Furthermore, because of their reliance on thrombus formation to achieve occlusion, these devices may have limited effectiveness in patients with a reduced ability to form blood clots, such as patients undergoing anti-coagulant therapy and/or thrombolytic therapy with tissue plasminogen activator (tPA), streptokinase, or a similar agent.

Occlusion of relatively large body vessels presents additional challenges for which prior art devices have proven insufficient. For example, occlusion devices with insufficient radial strength for maintaining a seal against a wall of a larger vessel can result in leakage around the perimeter of the occlusion device. Furthermore, with insufficient radial strength, the occlusion device can tilt or shift within the vessel over time, further impacting its ability to block fluid flow.

Accordingly, a need exists for improved occlusion devices for blocking fluid flow through bodily passages.

BRIEF SUMMARY OF DESCRIBED EMBODIMENTS

Several occlusion devices are described and illustrated herein.

A first exemplary occlusion device comprises a support frame comprising a disc-shaped member and a crossbar. The disc-shaped member defines a closed circumference and a central opening and includes a first coil defining a first passageway and a first core wire that extends through the first passageway. The crossbar is attached to the disc-shaped member and extends across the central opening. The crossbar includes a second coil that defines a second passageway and a second core wire that extends through the second passageway. A covering is attached to the support frame.

A second exemplary occlusion device comprises a first support frame, a first covering, a second support frame, and a second covering. The first support frame comprises a first disc-shaped member and a first crossbar. The first disc-shaped member has an outer edge and defines a closed circumference with a central opening. The first disc-shaped member includes a first coil defining a first passageway and a first core wire that extends through the first passageway. The first crossbar is attached to the first disc-shaped member and extends across the central opening. The first crossbar includes a second coil that defines a second passageway and a second core wire that extends through the second passageway. The first covering is attached to the first disc-shaped member and extends across the central opening of the first disc-shaped member. The second support frame is attached to the first support frame and comprises a second disc-shaped member and a second crossbar. The second disc-shaped member has an outer edge and defines a closed circumference with a central opening. The second disc-shaped member includes a third coil defining a third passageway and a third core wire that extends through the third passageway. The second crossbar is attached to the second disc-shaped member and extends across the central opening. The second crossbar includes a fourth coil that defines a fourth passageway and a fourth core wire that extends through the fourth passageway. The second covering is attached to the second disc-shaped member and extends across the central opening of the second disc-shaped member.

A third exemplary occlusion device comprises a first support frame, a first covering, a second support frame, and a second covering. The first support frame comprises a first disc-shaped member and a first crossbar. The first disc-shaped member has an outer edge and defines a closed circumference with a central opening. The first disc-shaped member includes a first coil defining a first passageway and a first portion of a common core wire that extends through the first passageway. The first crossbar is attached to the first disc-shaped member and extends across the central opening. The first crossbar includes a second coil that defines a second passageway and a second core wire that extends through the second passageway. The first covering is attached to the first disc-shaped member and extends across the central opening of the first disc-shaped member. The second support frame is attached to the first support frame and comprises a second disc-shaped member and a second crossbar. The second disc-shaped member has an outer edge and defines a closed circumference with a central opening. The second disc-shaped member includes a third coil defining a third passageway and a second portion of the common core wire that extends through the third passageway. The second crossbar is attached to the second disc-shaped member and extends across the central opening. The second crossbar includes a fourth coil that defines a fourth passageway and a fourth core wire that extends through the fourth passageway. The second covering is attached to the second disc-shaped member and extends across the central opening of the second disc-shaped member. The common core wire passes from the first support frame to the second support frame to attach the second support frame to the first support frame.

A fourth exemplary occlusion device comprises a first support frame, a first covering, a second support frame, and a second covering. The first support frame comprises a first disc-shaped member and a first crossbar. The first disc-shaped member has an outer edge and defines a closed circumference with a central opening. The first disc-shaped member includes a first coil defining a first passageway and a first portion of a common core wire that extends through the first passageway. The first crossbar is attached to the first disc-shaped member and extends across the central opening. The first crossbar includes a second coil that defines a second passageway and a second core wire that extends through the second passageway. The first covering is attached to the first disc-shaped member and extends across the central opening of the first disc-shaped member. The second support frame is attached to the first support frame and comprises a second disc-shaped member and a second crossbar. The second disc-shaped member has an outer edge and defines a closed circumference with a central opening. The second disc-shaped member includes a third coil defining a third passageway and a second portion of the common core wire that extends through the third passageway. The second crossbar is attached to the second disc-shaped member and extends across the central opening. The second crossbar includes a fourth coil that defines a fourth passageway and a fourth core wire that extends through the fourth passageway. The second covering is attached to the second disc-shaped member and extends across the central opening of the second disc-shaped member. The common core wire passes from the first support frame to the second support frame to attach the second support frame to the first support frame and passes through the first passageway and the third passageway multiple times.

Additional understanding of these exemplary occlusion devices can be obtained with review of the detailed description, below, and the appended drawings.

BRIEF DESCRIPTION OF THE DRAWINGS

FIG. 1 is a perspective view of a first exemplary occlusion device.

FIG. 2 is a perspective view of the occlusion device illustrated in FIG. 1. The occlusion device is illustrated in a resting configuration.

FIG. 8 is a partial sectional view of a bodily passage within which the first exemplary occlusion device has been deployed.

FIG. 9 is a partial section view of a bodily passage within which the first exemplary occlusion device has been deployed. A delivery and retrieval device is also positioned within the bodily passage.

FIG. 10 is a perspective view of a second exemplary occlusion device.

FIG. 22 is a side view of another exemplary occlusion device.

FIG. 23 is a side view of another exemplary occlusion device.

DETAILED DESCRIPTION OF DESCRIBED EMBODIMENTS

The following detailed description and the appended drawings describe and illustrate various exemplary devices and methods. The description and drawings are exemplary in nature and are provided to enable one skilled in the art to make and use one or more exemplary device and/or to practice one or more exemplary method. They are not intended to limit the scope of the claims in any manner.

Figure 3:
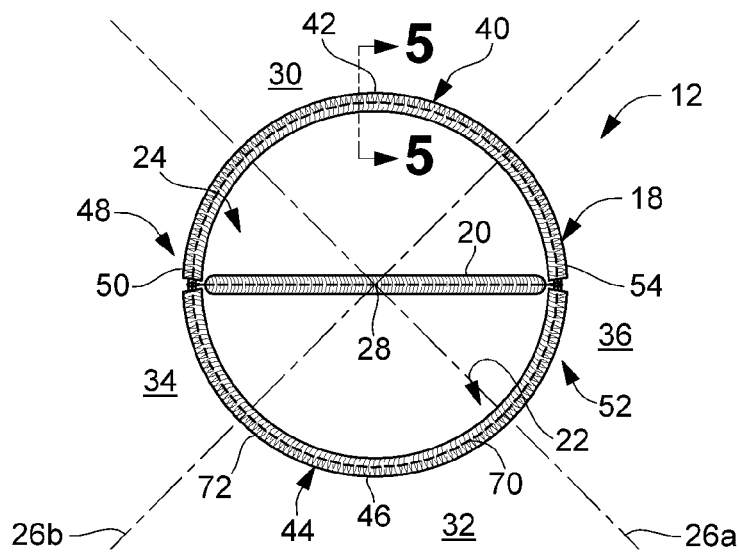
FIG. 3 is a perspective view of the support frame of the occlusion device illustrated in FIGS. 1 and 2.
Figure 4:
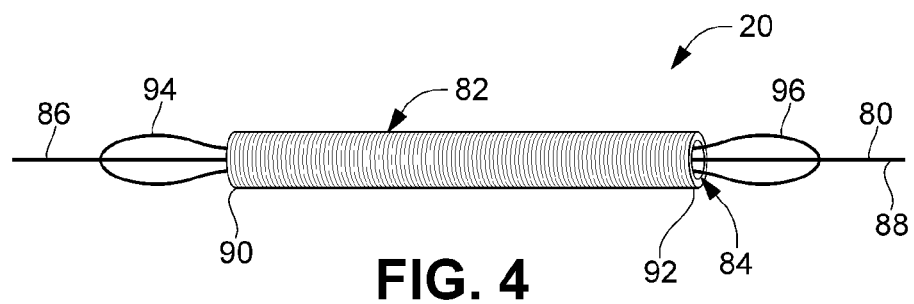
FIG. 4 is a perspective view of the crossbar of the support frame illustrated in FIG. 3.
Figure 5:
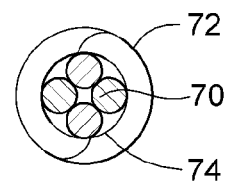
FIG. 5 is a sectional view of the support frame illustrated in FIG. 3, taken along line 5-5.
Figure 6:
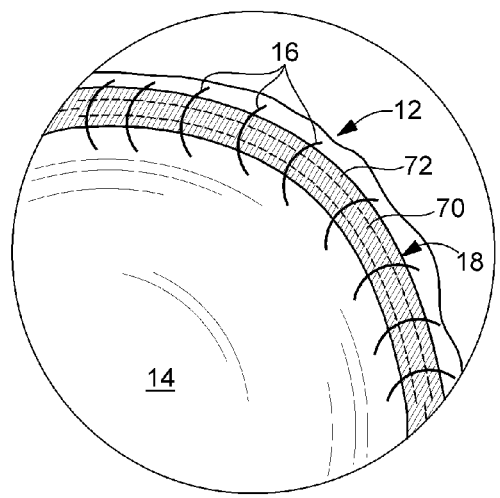
FIG. 6 is an enlarged view of the area indicated in FIG. 2.
Figure 7:
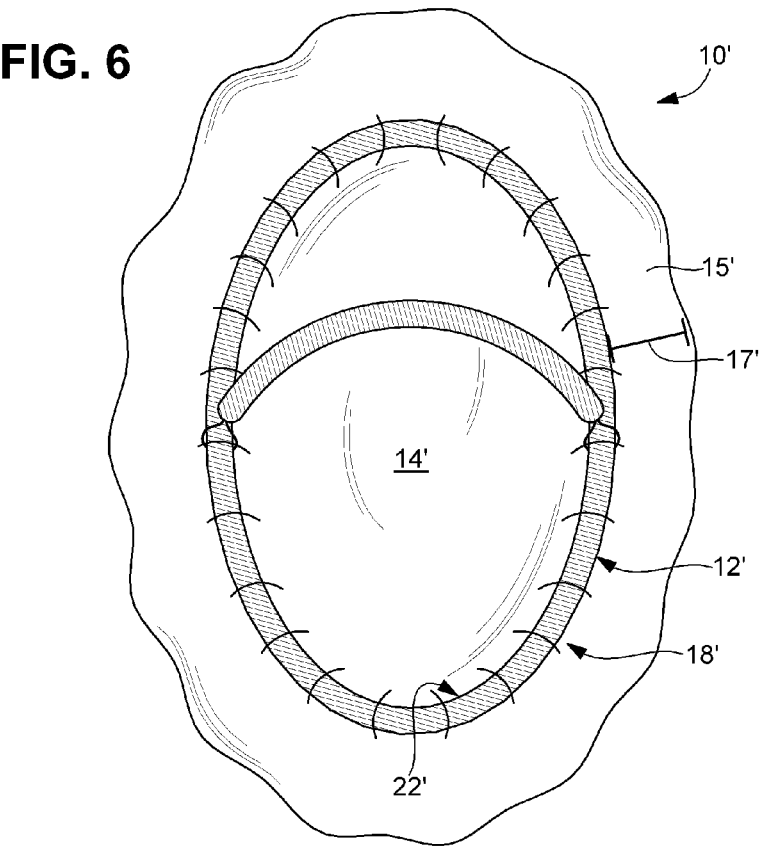
FIG. 7 is a perspective view of an alternative occlusion device.

FIGS. 1 through 9 relate to a first exemplary occlusion device. FIG. 1 illustrates the occlusion device 10 in a deployed configuration and FIG. 2 illustrates the occlusion device 10 in a resting configuration. FIGS. 3, 4, and 5 illustrate components of the occlusion device 10. FIG. 6 is an enlarged view of a portion of the occlusion device 10. FIG. 7 illustrates the occlusion device 10' according to an alternative construction. FIGS. 8 and 9 illustrate the occlusion device 10 deployed within a bodily passage 100.

The occlusion device 10 includes a support frame 12, a covering 14, and one or more attachment members 16 that attach the covering 14 to the support frame 12.

As best illustrated in FIG. 3, the support frame 12 comprises a disc-shaped member 18 and a crossbar 20. The disc-shaped member 18 has a closed circumference 22 that defines a central opening 24. The crossbar 20 is connected to the disc-shaped member 18 and spans the central opening 24. The covering 14 covers the entire central opening 24, effectively closing the opening 24.

Two lengthwise axes 26a, 26b that intersect at a geometric center 28 of the closed circumference 22 divide the disc-shaped member 18 into four quadrants: a top quadrant 30, a bottom quadrant 32 diametrically opposed from the top quadrant 30, a first lateral quadrant 34, and a second lateral quadrant 36 diametrically opposed from the first lateral quadrant 34. A first curve 40 defined by the disc-shaped member 18 in the top quadrant 30 defines a first apex 42. A second curve 44 defined by the disc-shaped member 18 in the bottom quadrant 32 defines a second apex 46. A third curve 48 defined by the disc-shaped member 18 in the first lateral quadrant 34 defines a third apex 50. A fourth curve 52 defined by the disc-shaped member 18 in the second lateral quadrant 36 defines a fourth apex 54.

FIG. 1 illustrates the occlusion device 10 in a first, or deployed, configuration 75. In the first configuration 75, the disc-shaped member 18 is folded such that the first apex 42 has been moved toward the second apex 46. Each of the third apex 50 and fourth apex 54 have flexed in response to this movement to form apical bends 56, 58. In the first configuration 75, the crossbar 20 defines a curve 60 that extends from the first apical bend 56 to the second apical bend 58 and away from the disc-shaped member 18. A curve 60 defined by the crossbar 20 when the occlusion device 10 is in the first configuration 75 defines an apex 62 that is positioned opposite the first 42 and second 46 apices relative to the geometric center of the disc-shaped member 18 (not specifically referenced in FIG. 1).

FIG. 2 illustrates the occlusion device 10 in a second, or resting, configuration 85. In the second configuration, the disc-shaped member 18 is substantially flat such that the entire support frame 12, including the disc-shaped member 18 and the crossbar 20, lies in a single plane. In this configuration, the first 42 and second 46 apices, and the third 50 and fourth 54 apices lie opposite each other with respect to the geometric center 28 of the disc-shaped member 18. As described below, the disc-shaped member 18 is configured to have sufficient flexibility to allow it to be readily transitioned between the first 75 and second 85 configurations. In the second configuration 85, the crossbar 20 extends across the central opening 24 of the disc-shaped member 18. While the crossbar 20 is not attached to the covering 14, some contact between the crossbar 20 and the covering may occur when the occlusion device 10 is in the second configuration 85.

The disc-shaped member 18 comprises a core wire 70 disposed within and extending through a lumen 74 formed by a coil 72. The core wire 70 is passed through the lumen 74 multiple times so that it loops back on itself in the same manner as described below for the crossbar 20. Once the desired number of passes is achieved, the ends of the core wire 70, which extend outward from opposite ends of the linear coil at this stage, are brought together to form the disc shape of the disc-shaped member 18. Once the disc shape is formed, the ends of the core wire 70 are tied or otherwise secured to each other to fix the disc shape of the disc-shaped member 18. The core wire 70 can be passed through the lumen 74 of the coil 72 any suitable number of times, and a skilled artisan will be able to select an appropriate number of passes based on various considerations, including the materials used for the core wire 70 and/or coil 72, the desired radial force of the disc-shaped member 18, and other considerations. The inventors have determined that a core wire 70 passed through the lumen 74 of a coil 72 four (4) times provides a disc-shaped member 18 with suitable properties when formed of a Nitinol core wire 70 and a cold drawn cobalt chromium coil 72. Furthermore, the inventors have determined that a core wire 70 passed through the lumen 74 of a coil 72 four (4) times provides a disc-shaped member 18 with suitable properties when formed of a Nitinol core wire 70 and a stainless steel coil 72.

It is noted that an occlusion device can have different components having coils with the same or different numbers of passes of a core wire through the respective lumen. For example, the inventors have determined that an occlusion device having a core wire passed through the lumen of a coil wire of a disc-shaped member four times and a core wire passed through the lumen of a coil of an attached crossbar four times has advantageous structural properties, particularly for relatively large occlusion devices, such as 14 mm devices. Also, the inventors have determined that an occlusion device having a core wire passed through the lumen of a coil wire of a disc-shaped member four times and a core wire passed through the lumen of a coil of a crossbar three times has advantageous structural properties, particularly for relatively small occlusion devices, such as 6, 8, 10, and 12 mm devices.

While the disc-shaped member is illustrated as comprising a single coil wire, separate coil wires can be used in the disc-shaped member. For example, separate coil wires with ends spaced from each other where the crossbar is attached to the core wire 70 can be used. This structural arrangement is considered advantageous for larger sized occlusion devices, such as 14 mm and larger devices. For these devices, the inclusion of two coil wires in the disc-shaped member is expected to eliminate a teardrop shape that can sometimes form in these larger-sized frames. It is noted, though, that while this structural arrangement is described as advantageous for larger sized devices, it is not considered necessary for these devices. Furthermore, this structural arrangement is considered suitable for inclusion in occlusion devices of all sizes.

The inclusion of multiple coil wires in the disc-shaped member is also considered advantageous at least because it allows for the use of a single core wire that passes through the coils of the multiple coil wires in the disc-shaped member and the coil of an attached crossbar. For example, each end of a crossbar can be positioned between ends of the separate coils of a disc-shaped member such that a core wire can be passed through the coils of the disc-shaped member and the coil of the crossbar. If desired, a second crossbar can be attached to the disc-shaped member in a similar manner or in any other suitable manner. The inventors have determined that an occlusion device having a disc-shaped member formed of two separate coils and a first crossbar attached to the disc-shaped member in this manner, e.g., via a common core wire passing through the coils forming the disc-shaped member and the coil forming the first crossbar, has advantageous structural properties, particularly for larger sized occlusion devices, such as 14 mm and larger devices. Furthermore, it is considered advantageous to have such a common core wire pass through the coils forming the disc-shaped member a total number of times that is equal to the total number of times that the common core wire passes through the coil of the first crossbar. For example, the inventors have determined that an occlusion device in which a common core wire passes through the coils forming the disc-shaped member four (4) times and through the coil of the first crossbar four (4) times has advantageous structural properties, particularly for larger sized occlusion devices, such as 14 mm and larger devices. Furthermore, if a second crossbar is attached to such an occlusion device, it can comprise a separate core wire passed through the lumen of its coil and be attached to the disc-shaped member using the separate core wire, as described above. If such a second crossbar is included, it is considered advantageous to have the separate core wire pass through the coil forming the second crossbar a total number of times that is less than the total number of times that the common core wire passes through the coil of the first crossbar. For example, the inventors have determined that, in an occlusion device in which a common core wire passes through the coils forming the disc-shaped member four (4) times and through the coil of the first crossbar four (4) times, a second crossbar attached to the disc-shaped member and having a separate core wire that passes through the lumen of its coil three (3) times provides advantageous structural properties when attached to the disc-shaped member, particularly for larger sized occlusion devices, such as 14 mm and larger devices.

The crossbar 20 has a construction that is similar to that of the disc-shaped member 18. As best illustrated in FIG. 4, the crossbar 20 comprises a core wire 80 disposed within and extending through a lumen 84 formed by a coil 82. For the crossbar 20, the core wire 80 is initially disposed within the lumen 84 such that each of the ends 86, 88 of the core wire 80 is disposed outward of the respective end 90, 92 of the coil 82. Each end 86, 88 of the core wire 80 is then passed back through the lumen 84 of the coil 82 until the end 86, 88 is disposed outward of the other end 90, 92 of the coil 82. As a result, the core wire 80 defines terminal loops 94, 96, each of which is disposed outward of an end 90, 92 of the coil 82. The construction of the crossbar 20 is similar to the construction of the anchors in United States Patent Application Publication No. 2010/0030246 to Pavcnik et al. for CLOSURE DEVICE AND METHOD FOR OCCLUDING A BODILY PASSAGEWAY, the entire contents of which is hereby incorporated into this disclosure.

As best illustrated in FIG. 3, the crossbar 20 is attached to the disc-shaped member 18 by looping the terminal loops 94, 96 of the core wire 80 of the crossbar 20 around the core wire 70 of the disc-shaped member 18. This can be accomplished during assembly of the crossbar 20, as described above, by passing each of the ends 86, 88 of the core wire 80 of the crossbar 20 around the core wire 70 of the disc-shaped member 18 at the desired points of connection, such as the third 50 and fourth 54 apices of the disc-shaped member 18, before passing the ends 86, 88 back through the coil 82. The ends 86, 88 can then be drawn taught on the core wire 70 of the disc-shaped member 18 to provide secure connections between the crossbar 20 and the disc-shaped member 18. Advantageously, the ends 86, 88 of the core wire 80 are drawn sufficiently taught such that each terminal loop 94, 96 frictionally engages the respective end 90, 92 of the coil 82 of the crossbar 20.

FIG. 4 illustrates the crossbar 20 independent of the disc-shaped member 18. Each of the ends 86, 88 of the core wire 80 of the crossbar 20 can extend axially beyond the respective end 90, 92 of the coil 82 by any suitable length. For example, each end 86, 88 can extend axially beyond the respective end 90, 92 of the coil 82 by a length that is less than, substantially less than, equal to, substantially equal to, greater than, or substantially greater than the axial length of the respective terminal loop 94, 96, as measured along a longitudinal axis of the crossbar 20 from the respective end 90, 92 of the coil to the apex of the respective terminal loop 94, 96. Configuring the crossbar 20 such that each of the ends 86, 88 of the core wire 80 extends axially beyond the respective end 90, 92 of the coil 82 by a length that is greater than or substantially greater than the axial length of the respective terminal loop 94, 96 is considered advantageous at least because ends 86, 88 configured in this manner can provide additional anchoring function to the occlusion device 10. Alternatively, a crossbar 20 in which each of the ends 86, 88 of the core wire 80 extends axially beyond the respective end 90, 92 of the coil 82 by a length that is less than or substantially less than the axial length of the respective terminal loop 94, 96 is considered advantageous at least because ends 86, 88 configured in this manner have limited ability to engage the covering 14. It may also be advantageous to configure the crossbar 20 such that each of the ends 86, 88 of the core wire 82 does not extend axially beyond the respective end 90, 92 of the coil 82. This configuration is believed to greatly reduce the ability of the ends 86, 88 to engage the covering 14.

The support frame 12 can be formed of any suitable material. The material selected for a support frame need only be biocompatible or able to be made biocompatible. Examples of suitable materials include, without limitation, stainless steel, nickel titanium (NiTi) alloys, e.g., nitinol, other shape memory and/or superelastic materials, molybdenum alloys, tantalum alloys, titanium alloys, paladium alloys, precious metals such as platinum, precious metal alloys such as platinum alloys, nickel chromium alloys, cobalt chromium alloys, nickel cobalt chromium alloys, nickel cobalt chromium molybdenum alloys, nickel titanium chromium alloys, linear elastic Nitinol wires, polymers, and composite materials.

Platinum and nitinol are currently considered desirable materials for use in the support frame due at least to their biocompatibility, shapeability, imaging characteristics, and well-characterized nature. Stainless steel is considered a suitable material for use in the support frame. Also, cold drawn cobalt chromium alloys, such as ASTM F562 and ASTM F1058 (commercial examples of which include MP35NTM and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials for use in the support frame at least because they are non-magnetic materials that provide beneficial magnetic resonance imaging (MRI) compatibility, and avoid MRI artifacts typically associated with some other materials, such as stainless steel.

Different materials can be used for the various components of the support frame 12. For example, the inventors have determined that the use of platinum for the coils 72, 82 and Nitinol for the core wires 70, 80 of the disc-shaped member 18 and the crossbar 20 provides a support frame with desirable characteristics, including desirable flexibility, manufacturability and handling characteristics. The inventors have determined that platinum coils provide desirable imaging characteristics for the support frame, including X-ray imaging characteristics, particularly when paired with a Nitinol core wire. The inventors have also determined that the use of cold drawn cobalt chromium, such as Elgiloy™ for the coils 72, 82 and nitinol for the core wires 70, 80 of the disc-shaped member 18 and the crossbar 20 provides a support frame with desirable characteristics, including desirable flexibility, manufacturability and handling characteristics.

Any suitable dimensions can be used for the various components of the support frame. A skilled artisan will be able to select suitable dimensions for the various components based on various considerations, including the point of treatment at which a particular occlusion device is intended to be used. The inventors have determined that it is advantageous to configure the support frame 12 such that the coil 82 of the crossbar 20 has a larger outer diameter than the coil 72 for the disc-shaped member 18 at least because the additional thickness provides additional material for use in retrieval and/or repositioning of the occlusion device 10 without adding significantly to the overall bulk of the occlusion device 10 because, when the device is in the first configuration 75, such as deployed within a vessel or positioned within a delivery device, the covering 14 and disc-shaped member 18 are axially separated from the crossbar 20. The inventors have determined that it is advantageous to configure the support frame 12 such that the core wire 80 of the crossbar 20, which can be formed of any suitable material (e.g., Nitinol), has a larger outer diameter than the core wire 70 for the disc-shaped member 18 when the coil 82 of the crossbar 20 has a larger outer diameter than the coil 72 for the disc-shaped member 18 at least because this improves the radial force of the device when in the deployed configuration. The inventors have determined that a coil 82 for the crossbar 20 having an outer diameter of 18 thousandths ($18/1000$) of an inch is considered suitable. Also, the inventors have determined that a coil 72 for the disc-shaped member 18 having an outer diameter of 14 thousandths ($14/1000$) of an inch is considered suitable. Used together, the coils 82, 72 having these dimensions provide an occlusion device that can be positioned within—and delivered with—a 4 or 5 French introducer sheath. The inventors have also determined that a core wire having an outer diameter of between 2 thousandths ($2/1000$) of an inch and 5 thousandths ($5/1000$) of an inch is considered suitable. A core wire having an outer diameter of 3 thousandths ($3/1000$) of an inch is considered particularly suitable. Furthermore, the inventors have determined that the combination of a coil wire having an outer diameter of 14 thousandths ($14/1000$) of an inch with a core wire having an outer diameter of 3 thousandths ($3/1000$) of an inch provides a support frame with desirable radial force and overall bulk characteristics, particularly when the core wire is passed through the lumen define by the coil wire three times.

It is noted that, as used herein, the term "wire" does not refer to any particular size, diameter, or cross-sectional shape. While wire members having substantially circular cross-sectional shapes offer particular advantages, they are not required. Examples of other suitable cross-sectional shapes include, but are not limited to, flat, square, triangular, D-shaped, trapezoidal, and delta-shaped cross-sectional shapes.

The inventors have determined that heat treating the support frame 12 can be advantageous at least because the occlusion device 10 has an improved ability to maintain its shape when a heat treatment has been applied to the support frame 12 during fabrication of the occlusion device 10. Furthermore, it is believed that heat treating the support frame 12 contributes to achieving the desired overall low profile of the occlusion device 10. In addition, it is considered advantageous to apply heat treatment during fabrication at least because this process sets the Af temperature of the support frame 12 such that it is more rigid at body temperature (e.g., has more radial force in the deployed configuration) than a support that is not heat treated. If a heat treatment is applied, any suitable treatment parameters can be used. A skilled artisan will be able to determine suitable parameters for a support frame in a particular occlusion device based on various considerations, including the materials used in the core wire and coil of the support frame. The inventors have determined that subjecting a support frame to a temperature of between about 880° F. and about 980° F. for between about 5 minutes and about 15 minutes, prior to attachment of a covering, provides these advantages for a support frame having a nitinol core wire and a coil formed of stainless steel or cold drawn cobalt chromium, such as Elgiloy™. The inventors have also determined that subjecting a support frame to a temperature of about 930° F. for about 5 minutes prior to attachment of a covering provides these advantages for a support frame having a nitinol core wire and a stainless steel coil.

As best illustrated in FIG. 6, the covering 14 is attached to the support frame 12 by one or more attachment members 16. In the illustrated embodiment, the attachment member 16 comprises a single suture that attaches the covering 14 to the disc-shaped member 18 of the support frame 12. When sutures are used as the attachment member 16, they advantageously extend through a thickness, such as a full thickness or a partial thickness, of the covering 14 and around the core wire 70 of the disc-shaped member 18. They can be drawn taught such that portions of the suture are disposed between turns of the coil 72. Alternatively, they can be drawn taught such that they are looped around the core wire 70 and the coil 72 of the disc-shaped member.

The attachment member 16 is advantageously configured such that the covering 14 and disc-shaped member 18 of the support frame 12 are maintained in continuous contact along the closed circumference 22 defined by the disc-shaped member 18. This continuous contact between the covering 14 and the disc-shaped member 18 is considered advantageous at least because it eliminates any gaps in contact between these elements that could provide an initial passageway through which fluid could flow across the occlusion device 10.

While sutures are considered suitable attachment members 16, any suitable attachment member can be used to connect the covering 14 to the support frame 12. Other examples of suitable attachment members include clips, clamps, staples and other attachment members known in the art. Furthermore, adhesives, welds, and other compositions and processes for forming a connection between members can be used. A skilled artisan will be able to select a suitable attachment member for attaching the covering 14 to the support frame 12 based on various considerations, including the nature of the covering 14 and the support frame 12 used in a particular occlusion device.

Also, while the use of a single attachment member 16, such as the single suture illustrated in the figures, is considered advantageous, any suitable number of attachment members can be used. A skilled artisan can select a suitable number of attachment members for use in a particular occlusion device based on various considerations, including the nature of the covering 14 and the support frame 12 used and the desirable continuous contact between the covering 14 and the disc-shaped member 18.

As best illustrated in FIG. 2, the covering 14 is advantageously sized and configured such that it defines an area that is substantially equal to the area defined by the closed circumference 22 of the disc-shaped member 18. This configuration minimizes the overall bulk of the occlusion device 10, enhancing its ability to be stored within and delivered by relatively small delivery catheters.

FIG. 7 illustrates an alternative occlusion device 10' in which the covering 14' is oversized relative to the closed circumference 22' defined by the disc-shaped member 18'. That is, the covering 14' is sized and configured such that it defines an area that is substantially greater than the area defined by the closed circumference 22' of the disc-shaped member 18'. The covering 14' provides a section of extra material 15' that extends radially beyond the outer edge of the disc-shaped member 18' relative to the geometric center (not specifically referenced in FIG. 7) of the disc-shaped member 18' when the occlusion device 10' is in the second configuration (such as illustrated in FIG. 7). The inclusion of the extra material 15' is considered advantageous at least because it provides additional material that, once the occlusion device 10' is deployed within a bodily passage, can contact and seal with the wall of the bodily passage. This structural arrangement upon deployment is expected to increase the effectiveness of the occlusion device 10' in blocking fluid flow through the bodily passage by providing additional surface area for contact with the wall of the bodily passage.

The covering 14' can be configured to have any suitable radial length 17' for the extra material 15' that extends radially beyond the outer edge of the disc-shaped member 18'. A skilled artisan can select a suitable radial length 17' for the extra material 15' based on various considerations, such as any size constraints placed on the overall bulk of the occlusion device 10' by a delivery device or intended point of treatment. The inclusion of the extra material 15' and the radial length 17' of any included extra material 15' should always be balanced against any considerations about the overall bulk of the occlusion device.

The inventors have determined that a radial length 17' that is between about 10% and about 90% of the radial length from the geometric center of the disc-shaped member 18' to the outer edge of the disc-shaped member is suitable for a variety of applications. A radial length 17' that is between about 20% and about 80% of the radial length from the geometric center of the disc-shaped member 18' to the outer edge of the disc-shaped member is suitable for a variety of applications. A radial length 17' that is between about 30% and about 70% of the radial length from the geometric center of the disc-shaped member 18' to the outer edge of the disc-shaped member is suitable for a variety of applications. A radial length 17' that is between about 40% and about 60% of the radial length from the geometric center of the disc-shaped member 18' to the outer edge of the disc-shaped member is suitable for a variety of applications. A radial length 17' that is about 50% of the radial length from the geometric center of the disc-shaped member 18' to the outer edge of the disc-shaped member is suitable for a variety of applications. A radial length 17' that is about 40% of the radial length from the geometric center of the disc-shaped member 18' to the outer edge of the disc-shaped member is suitable for a variety of applications. A radial length 17' that is about 30% of the radial length from the geometric center of the disc-shaped member 18' to the outer edge of the disc-shaped member is suitable for a variety of applications. A radial length 17' that is about 20% of the radial length from the geometric center of the disc-shaped member 18' to the outer edge of the disc-shaped member is suitable for a variety of applications. A radial length 17' that is about 10% of the radial length from the geometric center of the disc-shaped member 18' to the outer edge of the disc-shaped member is suitable for a variety of applications. A radial length 17' that is about 5% of the radial length from the geometric center of the disc-shaped member 18' to the outer edge of the disc-shaped member is suitable for a variety of applications.

If the extra material 15' is included, the covering 14' is advantageously sized and configured such that the radial length 17' is substantially uniform around the entire closed circumference 22' of the disc-shaped member 18'.

The covering 14 can be formed of any suitable material, and need only be biocompatible or be able to be rendered biocompatible. The material can advantageously be formed of a flexible material. Examples of suitable materials for the covering 14 include natural materials, synthetic materials, and combinations of natural and synthetic materials.

Examples of suitable natural materials include extracellular matrix (ECM) materials, such as small intestine submucosa (SIS), other bioremodellable materials, and fixed natural tissues, such as fixed bovine pericardium. Other examples of ECM materials that can be used in the occlusion device include stomach submucosa, liver basement membrane, urinary bladder submucosa, tissue mucosa, renal capsule, and dura mater. Dermis harvested from an animal, such as porcine dermis, or from another source, such as cadaveric dermis, is also considered a suitable natural material for the covering 14. Bioremodellable materials are particularly well-suited materials for use in the covering 14 at least because of their abilities to remodel and become incorporated into adjacent tissues. These materials can provide a scaffold onto which cellular in-growth can occur, eventually allowing the material to remodel into a structure of host cells. This ability to remodel into host tissue can allow occlusion devices that include such materials as the covering to provide permanent blockage of fluid flow through a bodily passage at a point where the occlusion device is deployed.

Examples of suitable synthetic materials include polymeric materials, such as thermoplastic polyethylene materials, expanded polytetrafluoroethylene (ePTFE), and other existing and later-developed polymeric materials considered suitable for use in implantable medical devices.

Ultra high molecular weight (UHMW) polymeric materials, such as UHMW thermoplastic materials, are considered well-suited for use in the covering at least because of the ability to prepare these materials as porous structures in various forms, including films, woven sheets, and non-woven sheets. UHMW polyethylene (UHMWPE, also known as high-modulus polyethylene (HMPE) or high-performance polyethylene (HPPE)) is considered particularly advantageous at least because of the ability to prepare this material as a thin film that retains fluid-blocking properties while not contributing significantly to the overall bulk of a device. The inventors have determined that UHMWPE materials having a micro-porous structure provide suitable materials for the covering. A micro-porous UHMWPE film having between about 40% and about 90% of the surface open, e.g., defined by pores, provides a particularly suitable material for the covering. Furthermore, the inventors have determined that a micro-porous UHMWPE film having pore sizes between about 0.05 micron and about 1.0 micron in diameter and a thickness between about 20 microns and about 120 microns provides a covering suitable for blocking fluid flow while having physical dimensions that contribute an acceptable level of bulk to the overall device. For porous materials, it is considered advantageous to use a material that provides a tortuous pore structure, such as a membrane having a fibrillar structure somewhat similar to a nonwoven material. Woven and non-woven sheets of UHMWPE having pore sizes that render the sheets porous to air but impervious to water are also considered suitable materials for the covering. It is noted, though, that a material that is permeable to fluid can be suitable for use in the covering if a covering, as a whole, formed of such material is able to block fluid flow as described herein. Furthermore, hydrophobic forms of UHMWPE are considered advantageous at least because it is expected that such materials will more effectively block fluid flow in some applications. Hydrophilic forms of UHMWPE are, however, also considered suitable for use.

A hydrophobic UHMWPE material that is impervious to fluid is considered advantageous at least because such materials are expected to contribute to the ability of an occlusion device to provide relatively quick closure following implantation.

The covering 14 can be processed in a manner that reduces the thickness of the material of the covering 14 as compared to non-processed material. Use of such materials can allow for reduction in the overall bulk of the occlusion device 10, which can allow the occlusion device 10 to be loaded into a delivery catheter having a relatively smaller French size. This, in turn, allows the occlusion device 10 to be delivered through and deployed within bodily passages of smaller inner diameter than those through which an occlusion device 10 having a covering 14 of relatively thicker material could be delivered. For example, the inventors have determined that the use of a covering 14 formed from an ECM material, such as SIS, that has been air-dried, stretched, and rehydrated prior to being attached to the support frame is advantageous at least because it provides a covering 14 that is thinner than an ECM that has not been processed in this manner. As a result, the occlusion device 10 has less overall bulk, allowing it to be loaded into smaller delivery catheters and deployed in bodily passages of smaller inner diameter.

For ECM coverings, any suitable procedure for air-drying, stretching, and/or rehydrating the covering can be used. The inventors have determined that an SIS covering can be suitably processed by laying the covering or a sheet containing the eventual covering flat in an open area, preferably in a sterile environment, allowing the covering to dry, gently stretching the dried covering, and rehydrating the covering with water for injection (WFI) or other suitable liquid. The rehydrated covering can then be attached to the support frame to make an occlusion device. The inventors have determined that, even after the rehydrating step, SIS processed in this manner does not swell to its original, pre-dried thickness. As a result, the processed covering has a reduced thickness that reduces the overall bulk of the finished occlusion device.

This approach—reducing the thickness or bulk of a component of the occlusion device—is contrary to a line of development taken in the art to increase effectiveness of occlusion devices. In many prior art devices, additional overall bulk has been added, such as by including a greater number of frame elements, for example, in an attempt to increase the ability of the occlusion device to occlude via thrombosis. As described more fully below, the inventors have surprisingly discovered that occlusion devices according to the disclosure demonstrate acceptable occlusion effectiveness despite efforts to reduce the overall bulk of the device, such as by using a covering that has been processed in a manner that reduces the thickness of the covering.

An example procedure considered suitable to stretch an ECM covering comprises attaching a hydrated covering to the disc-shaped member of a support frame such that it spans the closed circumference of the disc-shaped member, placing a load on a portion of the covering spanning the closed circumference of the disc-shaped member, and lyophilizing the covering while the load is being applied. For example, a sphere having a mass can be placed on a portion of the covering spanning the closed circumference of the disc-shaped member, which results in the covering stretching and deforming in response to the mass of the sphere. Subsequent lyophilization of the covering while the sphere is in contact with the covering advantageously imparts the stretched configuration onto the covering. Thus, the structural configuration of a covering can be configured based on the size of the load placed on the covering and the structural configuration of the load. While a sphere having a mass has been described as imparting a stretched configuration onto a covering, any suitable load having any suitable structural configuration can be placed on the covering using any suitable method, and skilled artisans will be able to select a suitable load, structural configuration for the load, and a suitable method for applying the load according to a particular embodiment based on various considerations, such as the desired structural configuration of the covering.

FIGS. 8 and 9 illustrate the occlusion device 10 deployed within a bodily passage 100. The occlusion device 10 has been deployed in the lumen 102 of the bodily passage 100 at a point of treatment where blockage of fluid flow, represented by arrow 106, is desired. The occlusion device 10 is in the first configuration 75 within the lumen 102. The disc-shaped member 18 has the first 42 and second 46 apices folded toward each other. As a result of tension placed on the disc-shaped member 18 by this folding, the member 18 exerts an outwardly-directed force as it seeks to return to the second, or resting, configuration (illustrated in FIG. 2). The outwardly-directed force forces the covering 14 to contact the wall 104 of the bodily passage 100, creating a seal between the covering 14 and the wall 104 and that extends around the entire perimeter of the covering 14. As such, the seal extends in a zig-zag pattern around the entire inner circumference of the wall 104 of the bodily passage 100. Together, the covering 14 and seal block fluid flow 106 from passing through the occlusion device 10.

Because the occlusion device 10 is in the first configuration 75, the crossbar 20 is disposed across the lumen 102 of the bodily passage 100 and defines curve 60 with apex 62. The curve 60 and apex 62 provide a structural feature that can be used for delivery and retrieval or repositioning of the occlusion device 10 following deployment. For example, as illustrated in FIG. 9, a catheter 101 with grasping arms 103, 105 can be used to engage the occlusion device 10 by grasping the curve 60 defined by the crossbar 20. The Mouse Tooth Retrieval Forceps, available from Cook Medical, is considered suitable for use in the delivery, retrieval and repositioning of the occlusion device 10.

The occlusion devices can be placed in a bodily passage using surgical, percutaneous delivery, or any other suitable placement technique. The occlusions devices are particularly well-suited, though, for placement using percutaneous delivery techniques. For example, an occlusion device can be placed in an appropriately-sized delivery catheter, navigated into a lumen of a bodily passage while in the delivery catheter, positioned at a desired point of treatment within the bodily passage, and deployed from the delivery catheter at the point of treatment. The delivery catheter can then be removed from the bodily passage, leaving the occlusion device at the point of treatment.

The occlusion devices can be placed in any suitable bodily passage, including arteries, veins, ducts, canals, and any other suitable passage where blockage of fluid flow is desired. The occlusion devices are considered particularly advantageous for placement in blood vessels, such as splenic, gastric, PCD, varicoceles, carotid, renal, femoral circumflex, deep femoral, iliac, and pulmonary blood vessels, for the blockage of blood flow therein. Also, as described above, the occlusion devices include various structural and other features that enable the devices to be navigated through and placed in bodily passages of relatively small size, such as blood vessels having internal diameters as small as 2.0 mm and as large as 8.5 mm or greater. The inventors have determined that it is advantageous to size the occlusion devices with between about 50% and about 300% oversizing, comparing the outer diameter of the disc-shaped member, after any heat treatment(s), to the inner diameter of the bodily passage. The inventors have determined that it is particularly advantageous to size the occlusion devices with between about 60% and about 150% oversizing, comparing the outer diameter of the disc-shaped member to the inner diameter of the bodily passage. The inventors have determined that it is particularly advantageous to size the occlusion devices with between about 65% and about 100% oversizing, comparing the outer diameter of the disc-shaped member to the inner diameter of the bodily passage. The inventors have determined that it is particularly advantageous to size the occlusion devices with about 66.6% oversizing, comparing the outer diameter of the disc-shaped member to the inner diameter of the bodily passage. The inventors have also determined that it is particularly advantageous to size the occlusion devices with about 100% oversizing, comparing the outer diameter of the disc-shaped member to the inner diameter of the bodily passage.

The occlusion device, or any portion thereof (e.g., support frame, covering, attachment members), can also comprise a bioactive. As used herein, the term "bioactive" refers to any composition that is believed to be capable of producing a biological and/or treatment effect in a host. The term includes compositions that directly produce biological effects, as well as compositions that produce, generate, or otherwise provide another composition that produces a biological effect. Further, the occlusion device can comprise two or more bioactives.

Any suitable bioactive can be used in the invention, and the specific bioactive chosen will depend on the desired effect. Examples of suitable bioactives include antithrombogenic agents, antiproliferative agents, and immunosuppressive agents. A wide range of other bioactives can be used, including heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin (Hytrin is a registered trademark of Abbott Laboratories Corporation of Abbott Park, Ill., USA) or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; tamoxifen citrate, Taxol (Taxol is a registered trademark of Bristol-Myers Squibb Company of New York, N.Y., USA) or the derivatives thereof, or other anti-cancer chemotherapeutic agents; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs; Proscar (Proscar is a registered trademark of Merck Sharp & Dohme Corporation of Whitehouse Station, N.J., USA), Hytrin (Hytrin is a registered trademark of Abbott Laboratories Corporation of Abbott Park, Ill., USA) or other agents for treating benign prostatic hyperplasia (BPH) or a mixture of any of these.

Further, in addition or as an alternative to the bioactives described above, any suitable thrombus-promoting substance, such as blood clotting factors, and/or thrombogenic material can be included on an occlusion device. Examples of suitable thrombus-promoting substances include, but are not limited to, thrombin, fibrinogen, and the like. Examples of suitable thrombogenic materials include, but are not limited to, coil fibers (e.g., polyester fibers), and sutures that promote thrombogenicity.

In some embodiments, the bioactive can comprise a bioactive capable of promoting healing and/or endothelialization (e.g., a peptide). A bioactive capable of promoting healing and/or endothelialization may have one or more desired treatment effects, including decreasing the propensity for recanalization.

If included, the bioactive can be associated with the occlusion device, or any portion thereof, in any suitable manner. For example, the bioactive can be coated on a surface of the occlusion device, disposed in a discrete portion of the occlusion device, and dispersed throughout a portion, or the entirety, of the occlusion device. The exact manner of associating the bioactive with the occlusion device will depend on numerous factors, which may include the nature of the bioactive and/or occlusion device, manufacturing methods, and desired treatment effect. Those skilled in the art can choose an appropriate manner of associating the bioactive with the occlusion device based on these and/or other factors.

The occlusion device may also comprise a barrier that controls release of the bioactive from the occlusion device. For example, the occlusion device can include a layer of the bioactive, either alone or with another material, and a barrier layer disposed on the bioactive layer. Also, the bioactive can be distributed in a barrier. In these embodiments, the barrier need only comprise a material that provides a controlled release of the bioactive from the occlusion device. For example, the barrier can be a polymer that controls release of the bioactive by diffusion of the bioactive through the polymer or degradation of the polymer. Furthermore, blends and layering of polymer(s) can be used to create a barrier. Examples of suitable arrangements of barriers are in U.S. Pat. No. 6,299,604 to Ragheb for a COATED IMPLANTABLE MEDICAL DEVICE, which is hereby incorporated by reference in its entirety.

FIG. 10 illustrates a second exemplary occlusion device 110. The occlusion device 110 is similar to the occlusion device 10 illustrated in FIG. 1 and described above, except as detailed below. Reference numbers in FIG. 10 refer to the same structural element or feature referenced by the same number in FIG. 1, offset by 100.

The occlusion device 110 includes a support frame 112, a covering 114, and one or more attachment members 116 that attach the covering 114 to the support frame 112. The support frame 112 comprises a disc-shaped member 118 and a crossbar 120. The disc-shaped member 118 has a closed circumference 122 that defines a central opening 124. The crossbar 120 is connected to the disc-shaped member 118 and spans the central opening 124.

The covering 114 includes a first portion 117 that is attached to the disc-shaped member 118 and a second portion 119 that is attached to the crossbar 120 and extends to the second curve 144 of the disc-shaped member 118. As illustrated in the FIG. 10, the second portion 119 is advantageously attached to the outside of the crossbar 120 and the outside of the second curve 144 of the disc-shaped member 118 to define a pocket 155 between the inner surfaces 121, 123 of the covering 114.

The inclusion of pocket 155 is considered advantageous at least because it is provides an additional barrier to fluid flow when the occlusion device 110 is deployed within a bodily passage. The second portion 119 of the covering 114 provides an outer surface 125 that can contact an inner surface of a wall of a bodily passage, which can provide an additional seal between the covering 114 and the wall. As illustrated in FIG. 10, the second portion 119 of the covering 114 includes slack that allows the second portion 119 to fit loosely on the support frame 112. The inclusion of a degree of slack in the second portion 119 is considered advantageous at least because it is expected to allow the second portion 119 to accommodate movement of fluid in the pocket 155, which may reduce stress on the second portion 119 and prevent the damage it may produce, such as tearing.

FIG. 10 illustrates the occlusion device 110 in a first, or deployed, configuration 175.

Figure 11:
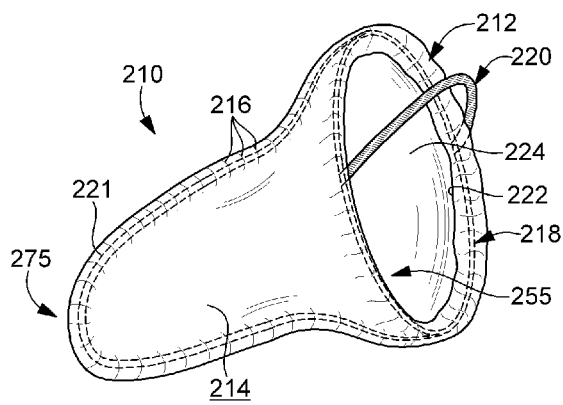
FIG. 11 is a perspective view of a third exemplary occlusion device.

FIG. 11 illustrates a third exemplary occlusion device 210. The occlusion device 210 is similar to the occlusion device 10 illustrated in FIG. 1 and described above, except as detailed below. Reference numbers in FIG. 11 refer to the same structural element or feature referenced by the same number in FIG. 1, offset by 200.

The occlusion device 210 includes a support frame 212, a covering 214, and one or more attachment members 216 that attach the covering 214 to the support frame 212. The support frame 212 comprises a disc-shaped member 218 and a crossbar 220. The disc-shaped member 218 has a closed circumference 222 that defines a central opening 224. The crossbar 220 is connected to the disc-shaped member 218 and spans the central opening 224.

The occlusion device 210 includes a second crossbar 221 that is connected to the disc-shaped member 218 and spans the central opening 224 defined by the disc-shaped member 218. The second crossbar 221 has a similar construction to that of the crossbar 220. The second crossbar 221 is has a greater length than that of the crossbar 220, though. As illustrated in FIG. 11, the second crossbar 221 is advantageously disposed orthogonally to the crossbar 220. That is, the second crossbar 221 lies in a plane that is perpendicular to or substantially perpendicular to a plane containing the crossbar 220. Also advantageously, the second crossbar 221 is attached to the disc-shaped member 218 at two points, each of which is spaced equidistant from the two attachment points where the crossbar 220 attaches to the disc-shaped member.

In the illustrated embodiment, the covering 214 extends over the second crossbar 221 so that the covering 214 is disposed radially outward of the second crossbar 221. This structural arrangement creates pocket 255 and is considered advantageous at least because it increases the surface area of the covering 214 that is exposed to fluid in the bodily passage. The increased surface area may increase the speed with which thrombus forms, which may enhance the effectiveness of the occlusion device 210 as compared to a device that lacks the pocket 255 and the additional surface area it provides for contact with the fluid in the bodily passage. The additional surface area of the covering 214 also provides additional material for contact with the wall of the bodily passage, which may enhance the effectiveness of the occlusion device 210 by providing a more extensive and/or stronger seal between the covering 214 and the bodily passage. The covering 214 can be attached to the second crossbar 221, such as with sutures or other suitable attachment mechanisms or means for attaching, or can be left free of attachment to the second crossbar 221.

FIG. 11 illustrates the occlusion device 210 in a first, or deployed, configuration 275.

Figure 12:
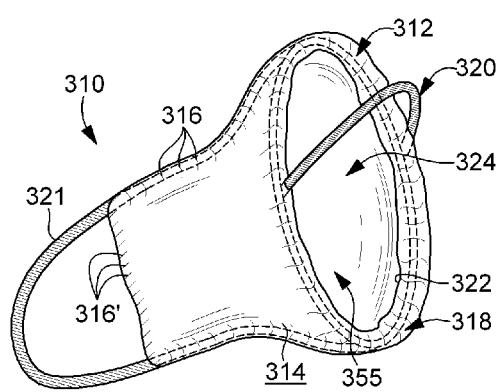
FIG. 12 is a perspective view of a fourth exemplary occlusion device.

FIG. 12 illustrates a fourth exemplary occlusion device 310. The occlusion device 310 is similar to the occlusion device 210 illustrated in FIG. 11 and described above, except as detailed below. Reference numbers in FIG. 12 refer to the same structural element or feature referenced by the same number in FIG. 11, offset by 100.

The occlusion device 310 includes a support frame 312, a covering 314, and one or more attachment members 316 that attach the covering 314 to the support frame 312. The support frame 312 comprises a disc-shaped member 318 and a crossbar 320. The disc-shaped member 318 has a closed circumference 322 that defines a central opening 324. The crossbar 320 is connected to the disc-shaped member 318 and spans the central opening 324.

The occlusion device 310 includes a second crossbar 321 that is connected to the disc-shaped member 318 and spans the central opening 324 defined by the disc-shaped member 318. The second crossbar 321 has a similar construction to that of the crossbar 320. The second crossbar 321 is has a greater length than that of the crossbar 320, though. As illustrated in FIG. 12, the second crossbar 321 is advantageously disposed orthogonally to the crossbar 320. That is, the second crossbar 321 lies in a plane that is perpendicular to or substantially perpendicular to a plane containing the crossbar 320. Also advantageously, the second crossbar 321 is attached to the disc-shaped member 318 at two points, each of which is spaced equidistant from the two attachment points where the crossbar 320 attaches to the disc-shaped member.

In the illustrated embodiment, the covering 314 extends over the second crossbar 321 so that the covering 314 is disposed radially outward of the second crossbar 321. In this embodiment, the covering 314 does not extend along the entire length of the second crossbar 321, creating a terminal portion of the second crossbar 321 that is not covered by the covering 314. The terminal end of the covering 314 is sealed closed, such as by additional attachment members 316' that secure opposing surfaces of the covering 314 to each other.

While this structural arrangement creates a pocket 355 that has a shorter longitudinal length than the pocket 255 in the occlusion device 210 illustrated in FIG. 11, this arrangement can be advantageous at least because it exposes a portion of the second crossbar 321 that can be used for engagement with a retrieval and/or repositioning device, which may avoid potential damage to the covering 314 by such devices. This arrangement can also lower the overall profile of the occlusion device 310. Furthermore, this arrangement may reduce or eliminate any stresses that may be placed on a covering that extends over the second crossbar, such as covering 214 in the embodiment illustrated in FIG. 11.

In making an occlusion device according to a particular embodiment, a skilled artisan can balance the expected advantages of the embodiment illustrated in FIG. 11 and described above (e.g., the depth of the pocket 255 provides additional surface area for thrombus formation and contact with the wall of the bodily passage) against the expected advantages of the embodiment illustrated in FIG. 12 (e.g., the relatively low profile nature of the occlusion device 310 and the elimination of stresses on the covering 314).

Figure 13:
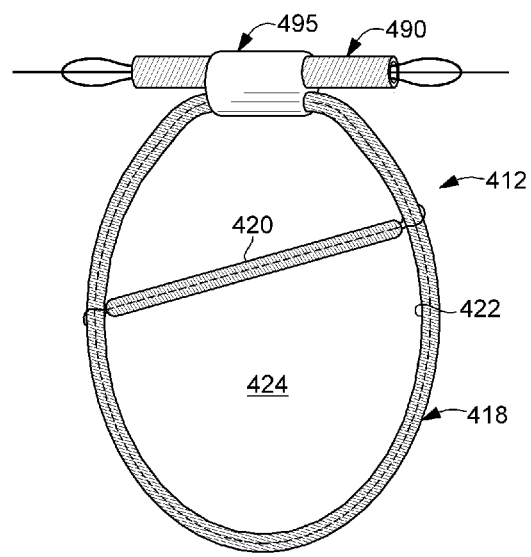
FIG. 13 is a perspective view of an alternative support frame for use in occlusion devices.

FIG. 13 illustrates an alternative support frame 412 for use in occlusion devices. The support frame 412 is similar to the support frames described in connection with other occlusion devices described herein, except as detailed below. Thus, the support frame 412 includes a disc-shaped member 418 formed of a core wire and a coil, and a crossbar 420 formed of a core wire and a coil. The disc-shaped member 418 defines a closed circumference 422 and a central opening 424.

An anchor 490 is attached to the disc-shaped member 418 by cannula 495. Any other suitable means for attaching can be used, but cannula 495 is considered advantageous at least because of the ease it provides in attaching the anchor 490 to the disc-shaped member 418. The anchor 490, in essence, is another crossbar. The ends of the core wire provide barb that can facilitate anchoring of an occlusion device in a bodily passage.

Figure 14:
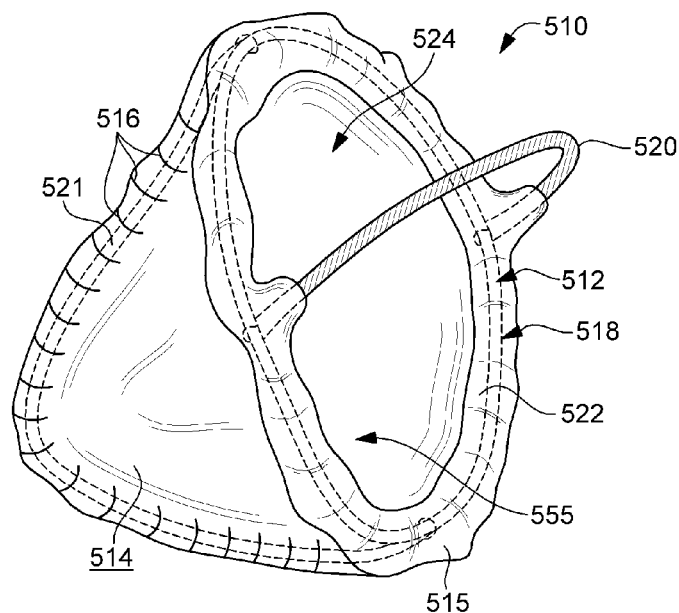
FIG. 14 is a perspective view of a fifth exemplary occlusion device.

FIG. 14 illustrates a fifth exemplary occlusion device 510. The occlusion device 510 is similar to the occlusion device 10 illustrated in FIG. 1 and described above, except as detailed below. Reference numbers in FIG. 14 refer to the same structural element or feature referenced by the same number in FIG. 1, offset by 500.

The occlusion device 510 includes a support frame 512, a covering 514, and one or more attachment members 516 that attach the covering 514 to the support frame 512. The support frame 512 comprises a disc-shaped member 518 and a crossbar 520. The disc-shaped member 518 has a closed circumference 522 that defines a central opening 524. The crossbar 520 is connected to the disc-shaped member 518 and spans the central opening 524.

The occlusion device 510 includes a second crossbar 521 that is connected to the disc-shaped member 518 and spans the central opening 524 defined by the disc-shaped member 518. The second crossbar 521 has a similar construction to that of the crossbar 520. In this embodiment, the crossbar 520 and the second crossbar 521 have the same longitudinal length or substantially the same longitudinal length. As illustrated in FIG. 14, the second crossbar 521 is advantageously disposed orthogonally or substantially orthogonally to the crossbar 520. That is, the second crossbar 521 lies in a plane that is perpendicular to or substantially perpendicular to a plane containing the crossbar 520. Also advantageously, the second crossbar 521 is attached to the disc-shaped member 518 at two points, each of which is spaced equidistant from the two attachment points where the crossbar 520 attaches to the disc-shaped member 518.

In the illustrated embodiment, the covering 514 extends over the second crossbar 521 so that the covering 514 is disposed radially outward of the second crossbar 521. This structural arrangement creates pocket 355 and is considered advantageous at least because it increases the surface area of the covering 314 that is exposed to fluid in the bodily passage.

The covering 514 can be free of attachment to second crossbar 521, as illustrated in FIG. 14. Alternatively, the covering 514 can be attached to the second crossbar 521 using any suitable attachment members, such as sutures, clips, bonds, welds, and any other suitable structure, process, and/ or technique for attaching a covering material to a frame. Attachment of the covering 514 to the second crossbar 521 in this manner is considered advantageous at least because it is expected to minimize movement of a free covering 514 within the body vessel following implantation, which may enhance the chronic performance of the occlusion device 510.

The covering 514 provides a section of extra material 515 that extends radially beyond the outer edge of the disc-shaped member 518 relative to the geometric center (not specifically referenced in FIG. 14) of the disc-shaped member 518 when the occlusion device 510 is in the first configuration (such as illustrated in FIG. 14). The inclusion of the extra material 515 is considered advantageous at least because it provides additional material that, once the occlusion device 510 is deployed within a bodily passage, can contact and seal with the wall of the bodily passage. This structural arrangement upon deployment is expected to increase the effectiveness of the occlusion device 510 in blocking fluid flow through the bodily passage by providing additional surface area for contact with the wall of the bodily passage.

FIG. 14 illustrates the occlusion device 510 in a first, or deployed, configuration.

Figure 15:
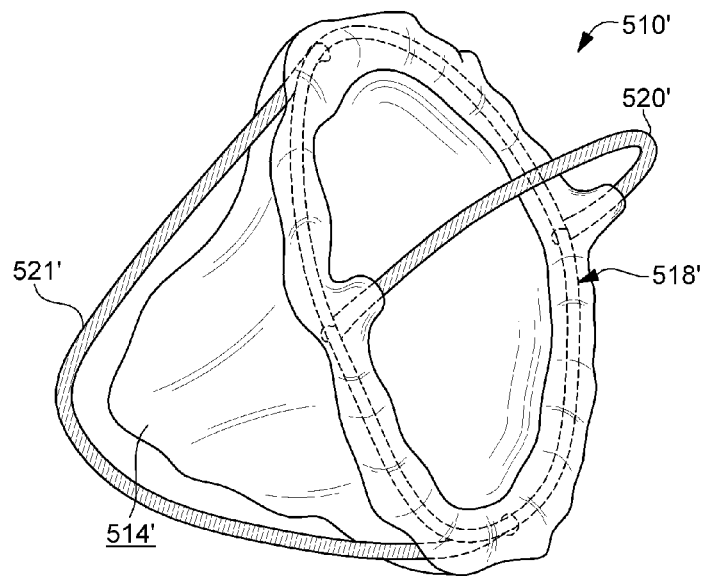
FIG. 15 is a perspective view of an alternative occlusion device.

FIG. 15 illustrates the fifth exemplary occlusion device 510' according to an alternative construction. The occlusion device 510' according to this alternative embodiment is similar to the occlusion device 510 illustrated in FIG. 14 and described above, except as indicated below. In this alternative embodiment, the covering 514' is disposed radially inward of the second crossbar 521', i.e., closer to a geometric center of the disc-shaped member 518' than the second crossbar 521'. This structural arrangement is expected to allow a user to position the occlusion device 510' in either orientation within the bodily passage (i.e., with either the crossbar 520' or the second crossbar 521' upstream within the passage, and, as a result, with either the crossbar 520' or the second crossbar 521' downstream in the passage). This is expected to eliminate any need to confirm that the occlusion device 510' is positioned in a delivery catheter properly prior to placement within a bodily passage.

Similar to the embodiment illustrated in FIG. 14 and described above, the covering 514' can be free of attachment to second crossbar 521', as illustrated in FIG. 15. Alternatively, the covering 514' can be attached to the second crossbar 521' using any suitable attachment members, such as sutures, clips, bonds, welds, and any other suitable structure, process, and/or technique for attaching a covering material to a frame. Attachment of the covering 514' to the second crossbar 521' in this manner is considered advantageous at least because it is expected to minimize movement of a free covering 514' within the body vessel and, in this embodiment, within the frame, following implantation, which may enhance the chronic performance of the occlusion device 510'.

Figure 16:
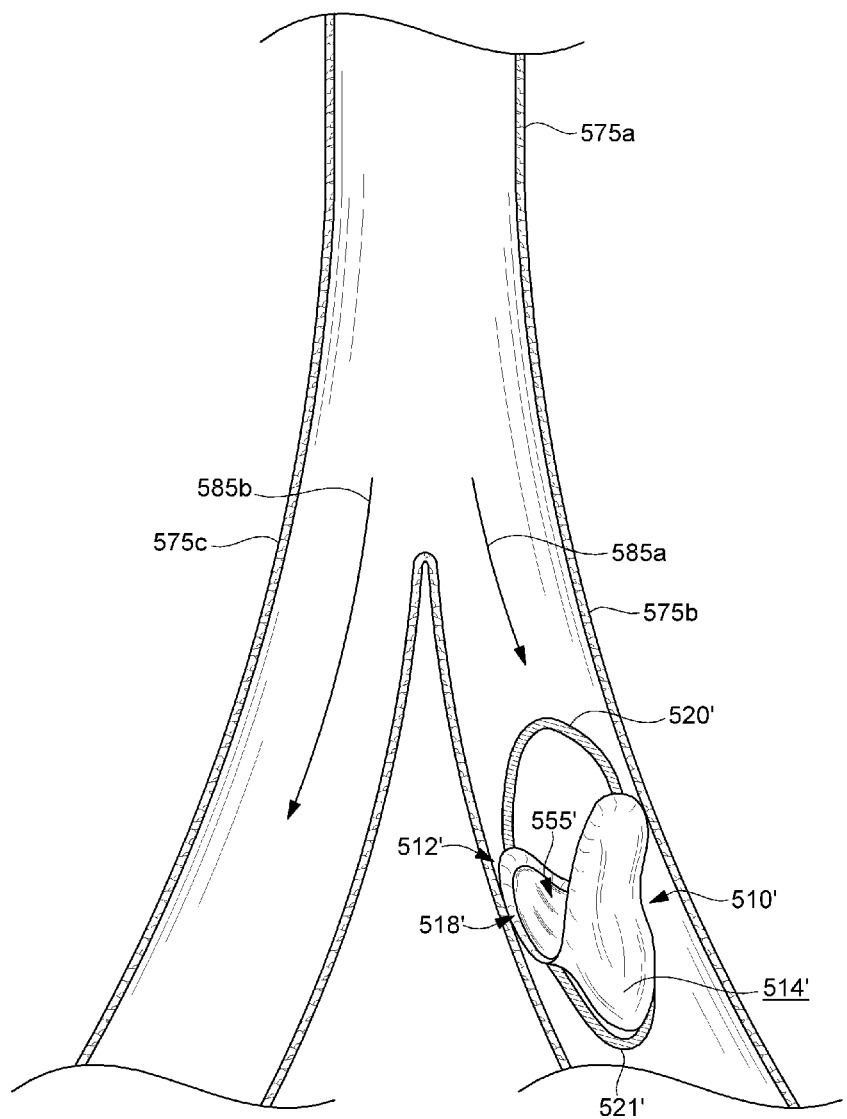
FIG. 16 is an oblique view of a bodily passage within which an exemplary occlusion device has been implanted.

FIG. 16 illustrates the occlusion device 510' implanted in an external iliac artery 575b of a human being. The disc-shaped member 518' has adopted a sinusoidal configuration as a result of the oversizing of the support frame 512' relative to the inner diameter of the artery 575b. The crossbar 520' extends away from the disc-shaped member 518' in a proximal direction, and the second crossbar 521' extends away from the disc-shaped member 518' in a substantially opposite, distal direction. The covering 514' extends distally away from the disc-shaped member 518' and defines pocket 555'. The covering also forms a circumferential seal with the internal wall of the iliac artery 575b. The occlusion device 510' is positioned to block fluid flowing distally in the external iliac artery 575b, represented by arrow 585a. Fluid flowing distally through the common iliac artery 575a is still able to pass through the internal iliac artery 575c, represented by arrow 585b.

Figure 17:
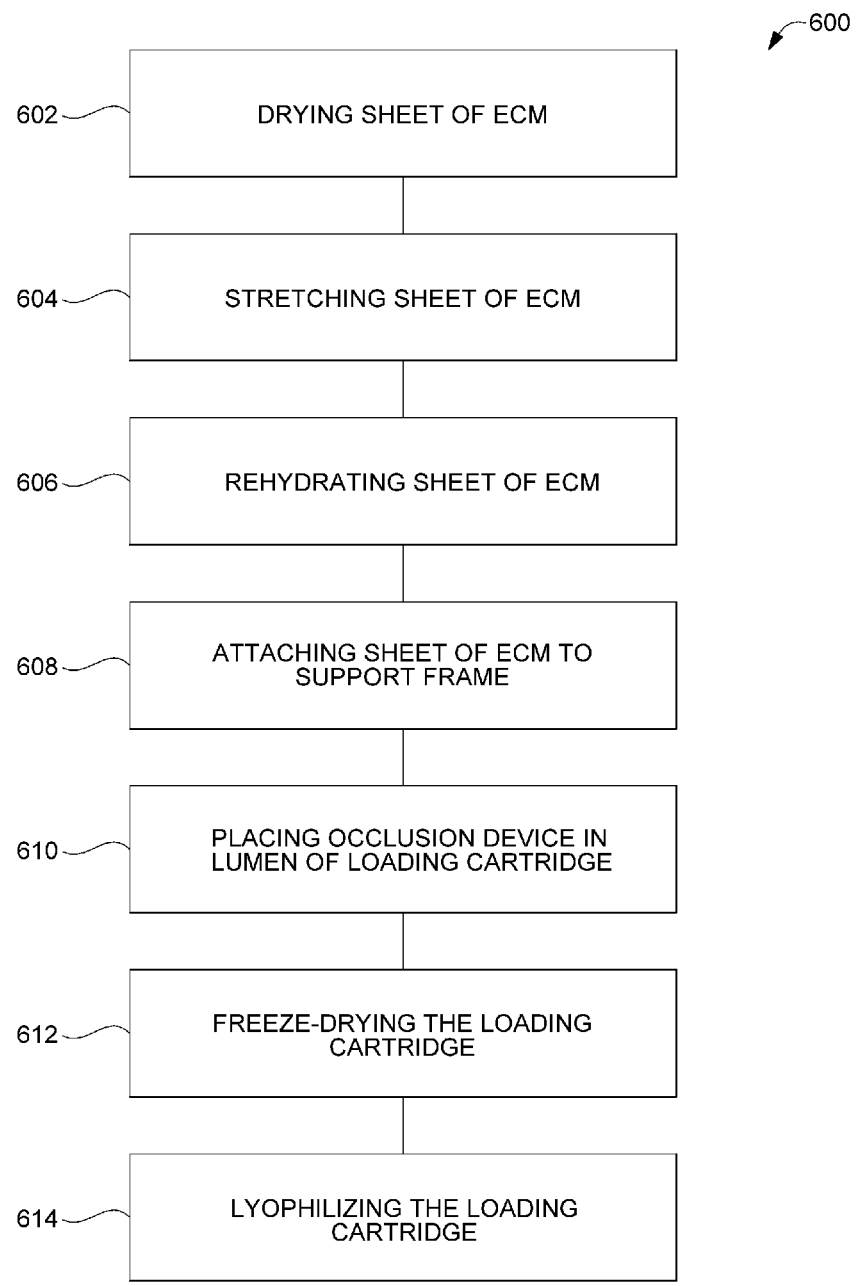
FIG. 17 is a flowchart illustrating an exemplary method of making an occlusion device.

FIG. 17 illustrates an exemplary method 600 of making an occlusion device. In an initial step 602, a sheet of ECM, such as SIS, is air dried. In another step 604, the sheet is stretched.

In another step 606, the sheet is rehydrated. In another step 608, the sheet is attached to a support frame comprising a disc-shaped member and a crossbar in accordance with the disclosure to produce an occlusion device having a support frame and a covering. In another step 610, the occlusion device is placed into the lumen of a loading cartridge comprising an elongate tubular member, such as a sheath having a peel-away structure. The tubular member advantageously includes a series of holes to aid in the drying and rehydration steps below. In another step 612, the loading cartridge, containing the occlusion device, is freeze-dried. In another step 614, the loading cartridge, containing the occlusion device, is lyophilized. The inclusion of a lyophilization step is advantageous at least because it helps ensure that the covering does not adhere to itself. This is considered particularly advantageous for coverings formed of SIS and other ECMs.

Immediately prior to use, the occlusion device can be rehydrated and transferred into an appropriately-sized delivery sheath.

Figure 18:
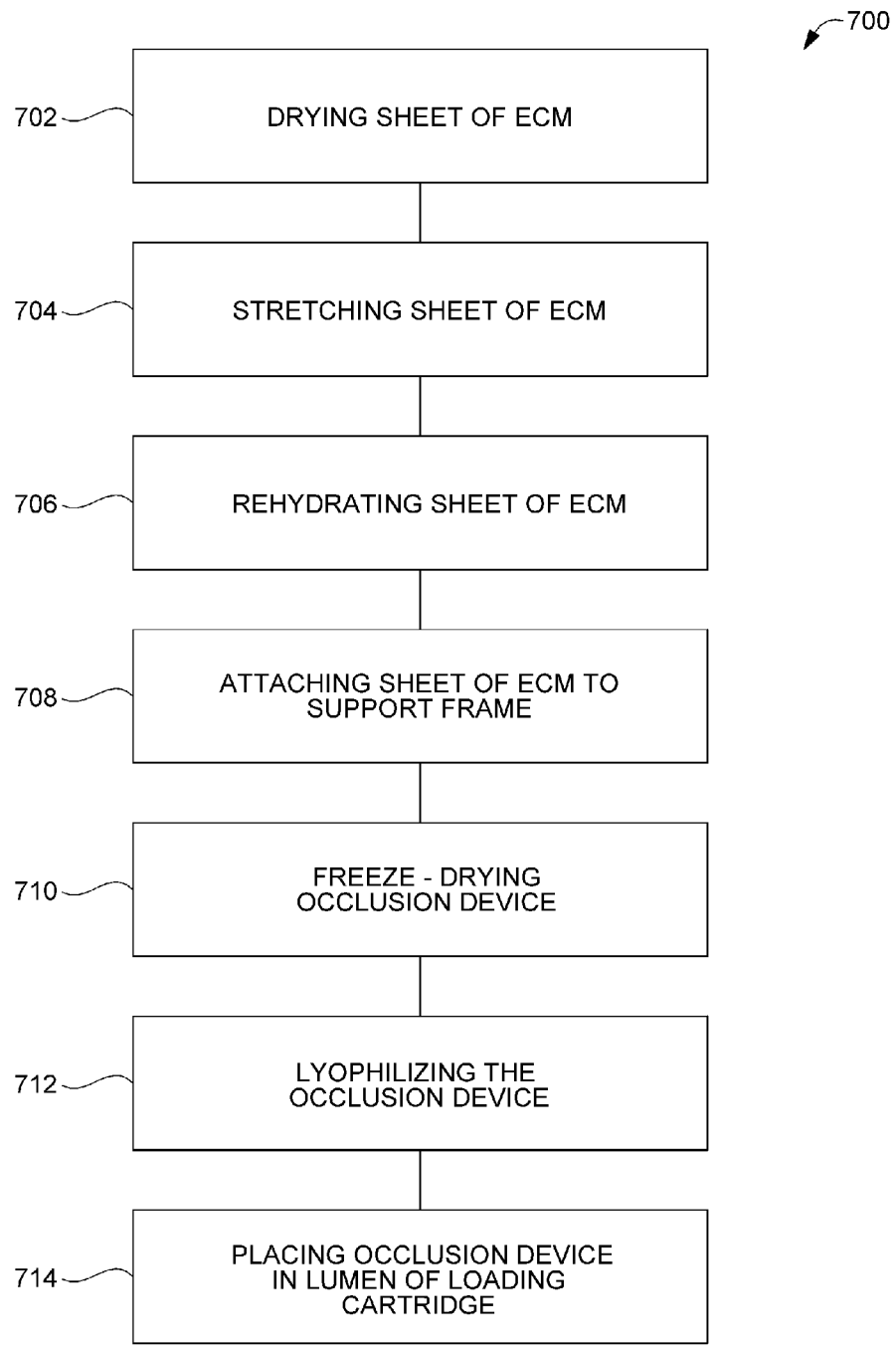
FIG. 18 is a flowchart illustrating a second exemplary method of making an occlusion device.

FIG. 18 illustrates a second exemplary method 700 of making an occlusion device. In an initial step 702, a sheet of ECM, such as SIS, is air dried. In another step 704, the sheet is stretched. In another step 706, the sheet is rehydrated. In another step 708, the sheet is attached to a support frame comprising a disc-shaped member and a crossbar in accordance with the disclosure to produce an occlusion device having a support frame and a covering. In another step 710 the occlusion device is freeze-dried in an open, resting, configuration. In another step 712 the occlusion device is lyophilized in an open, resting, configuration. In another step 714, the occlusion device is placed into the lumen of a loading cartridge comprising an elongate tubular member, such as a sheath having a peel-away structure. The occlusion device is placed into the lumen of a loading cartridge in an open, resting, configuration. The tubular member advantageously includes a series of holes to aid in the rehydration step below. Optionally, the step 710 of freeze-drying the occlusion device and the step 712 of lyophilizing the occlusion device can be omitted from the above methodology.

Immediately prior to use, the occlusion device can be rehydrated and transferred into an appropriately-sized delivery sheath.

Multi-Stage Occlusion Devices

The inventors have determined that the various single-stage occlusion devices—devices including a single disc-shaped member—described herein are particularly well-suited for use in relatively small body vessels less, i.e., body vessels having an inner diameter of less than 6 mm. The inventors have determined, however, that larger body vessels, i.e., body vessels having an inner diameter of 6 mm or greater, present additional challenges in achieving occlusion. For example, larger body vessels may present greater fluid flow and pressures than smaller body vessels. To address these challenges, the inventors have developed multi-stage occlusion devices—devices including multiple disc-shaped members that effectively occlude these larger body vessels. Various exemplary structures for these multi-stage occlusion devices are described below and illustrated in the appended drawings.

Figure 19:
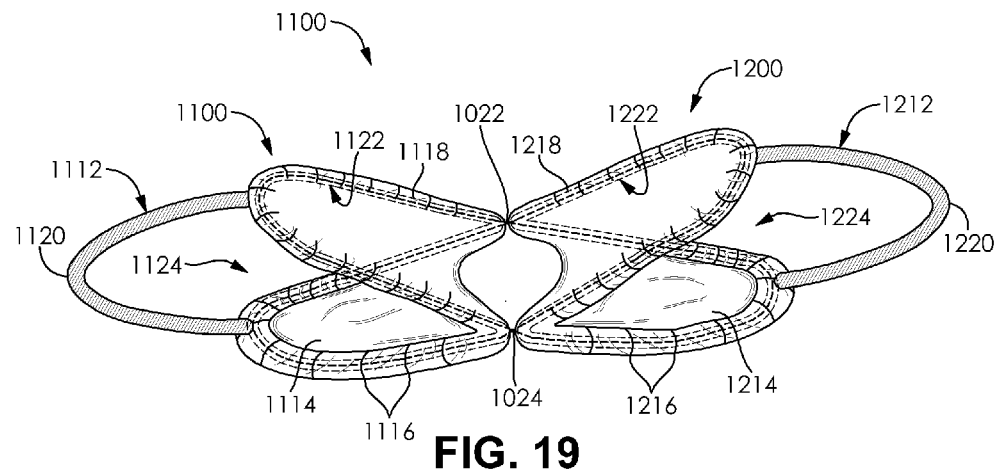
FIG. 19 is a perspective view of another exemplary occlusion device.
Figure 20:
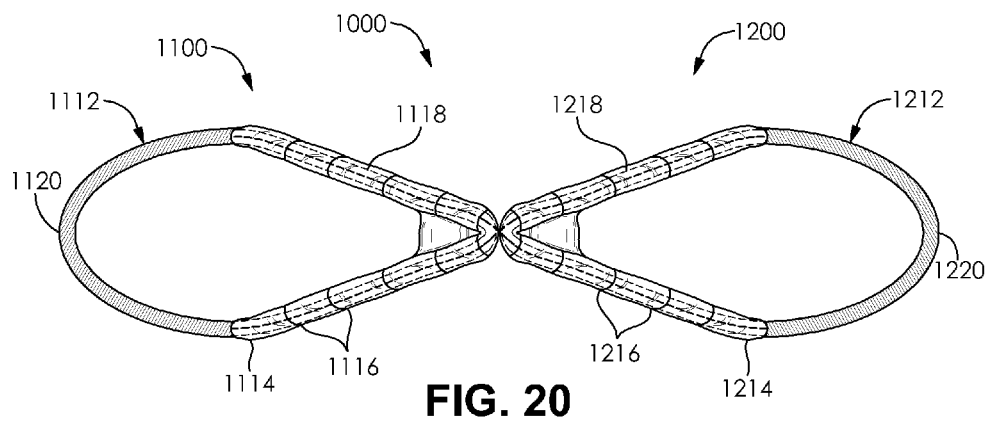
FIG. 20 is a side view of the occlusion device illustrated in FIG. 19.
Figure 21A:
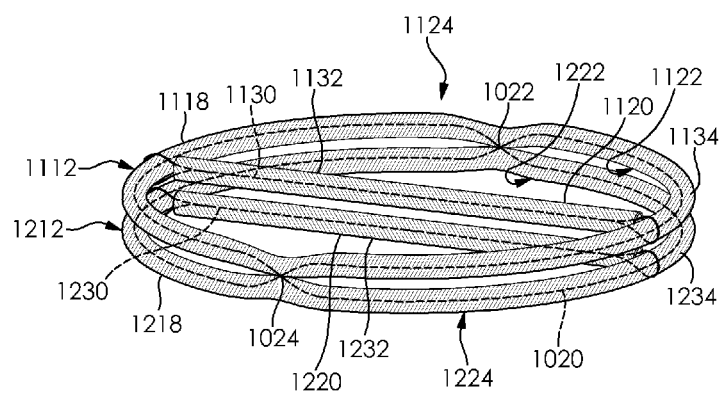
FIG. 21A is a perspective view of the support frame of the occlusion device illustrated in FIGS. 19 and 20. The support frame is illustrated in a first configuration.
Figure 21B:
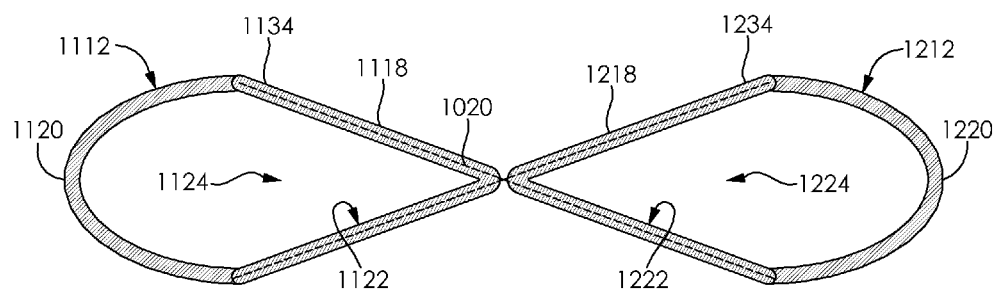
FIG. 21B is a side view of the support frame of the occlusion device illustrated in FIGS. 19 and 20. The support frame is illustrated in a second configuration.

FIGS. 19, 20, 21A and 21B relate to first exemplary multi-stage occlusion device 1000. FIGS. 19 and 20 illustrate the occlusion device 1000 in a deployed configuration; FIGS. 21A and 21B illustrate the support frame components 1112, 1212 of the occlusion device 1000 independent of other components.

The occlusion device 1000 has first 1100 and second 1200 axially adjacent stages. The first stage 1100 includes a first support frame 1112, a first covering 1114, and a first set of one or more attachment members 1116 that attach the first covering 1114 to the first support frame 1112. Similarly, the second stage 1200 includes a second support frame 1212, a second covering 1214, and a second set of one or more attachment members 1216 that attach the second covering 1214 to the second support frame 1212.

Each support frame 1112, 1212 can have any suitable structural configuration. A skilled artisan will be able to select an appropriate construction for the support frames in a multi-stage occlusion device according to a particular embodiment based on various considerations, including the nature of the material being used for the for the support frame. For example, frames comprising a unitary structure formed of wire or cut from a sheet or tube can be used.

As best illustrated in FIG. 21A, exemplary multi-stage occlusion device 1000 includes support frames 1112, 1212 that each include a disc-shaped member 1118, 1218 and a crossbar 1120, 1220 constructed and arranged in accordance with the support frame component of the first exemplary single-stage occlusion device described above and illustrated in FIG. 3. Thus, the first support frame 1112 comprises a first disc-shaped member 1118 and a first crossbar 1120. The first disc-shaped member 1118 has a first closed circumference 1122 that defines a first central opening 1124. The first crossbar 1120 is connected to the first disc-shaped member 1118 and spans the first central opening 1124. The first covering 1114 is attached to the first disc-shaped member 1118 by a first set of one or more attachment members 1116 such that the first covering 1114 covers the entire first central opening 1124, effectively closing the first opening 1124. Similarly, the second support frame 1212 comprises a second disc-shaped member 1218 and a second crossbar 1220. The second disc-shaped member 1218 has a second closed circumference 1222 that defines a second central opening 1224. The second crossbar 1220 is connected to the second disc-shaped member 1218 and spans the second central opening 1224. The second covering 1214 is attached to the second disc-shaped member 1218 by a second set of one or more attachment members 1216 such that the second covering 1214 covers the entire second central opening 1224, effectively closing the second opening 1224.

In the illustrated embodiment, the first covering 1114 is free, or substantially free, of contact with the first crossbar 1120, excluding only minimal contact that might occur at the attachment points of the first crossbar 1120 to the first disc-shaped member 1118. Thus, the first crossbar 1120 extends over the first covering 1114 from one side of the first disc-shaped member 1118 to an opposite side of the first disc-shaped member 1118. The first covering 1114, therefore, is attached to the first disc-shaped member 1118 such that it lies under, or extends under, the first crossbar 1120 and is free of attachment to the first crossbar 1120.

In the illustrated embodiment, the second covering 1214 is free, or substantially free, of contact with the second crossbar 1220, excluding only minimal contact that might occur at the attachment points of the second crossbar 1220 to the second disc-shaped member 1218. Thus, the second crossbar 1220 extends over the second covering 1214 from one side of the second disc-shaped member 1218 to an opposite side of the second disc-shaped member 1218. The second covering 1214, therefore, is attached to the second disc-shaped member 1218 such that it lies under, or extends under, the second crossbar 1220 and is free of attachment to the second crossbar 1220.

In this multi-stage embodiment, each of the crossbars 1120, 1220 advantageously has a length that is less than the diameter of the disc-shaped member 1118, 1218 to which it is attached when the disc-shaped member is in a resting configuration. The inventors have determined that the structural arrangement provided by inclusion of crossbars 1120, 1220 having such a configuration relative to the appropriate disc-shaped members is advantageous at least because this structural arrangement allows the respective support frame 1112, 1212 to exert greater radial force when placed in the deployed configuration than if the crossbar 1118, 1218 had another length relative to the diameter of the respective disc-shaped member 1118, 1218. Any crossbar length that is less than the diameter of the disc-shaped member to which the crossbar is attached when the disc-shaped member is in a resting configuration is considered suitable. A skilled artisan will be able to select appropriate lengths for crossbars in a multi-stage occlusion device according to a particular embodiment based on various considerations, including the size of the disc-shaped members to which the crossbars will be attached, the size of the body vessel within which the multi-stage occlusion device is intended to be deployed, and any considerations regarding the overall bulk of the multi-stage occlusion device and any delivery system that will be used to deploy the device. The inventors have determined that a crossbar having a length that is between approximately 50% and approximately 99% of the diameter of the disc-shaped member, when in a resting configuration, to which the crossbar will be attached provides a desirable balance between considerations regarding the radial force of the multi-stage occlusion device and the overall bulk of the device. The inventors have determined that a crossbar having a length that is between approximately 60% and approximately 90% of the diameter of the disc-shaped member, when in a resting configuration, to which the crossbar will be attached provides an advantageous configuration for relatively large body vessels. Similarly, the inventors have determined that a crossbar having a length that is between approximately 70% and approximately 80% of the diameter of the disc-shaped member, when in a resting configuration, to which the crossbar will be attached provides an advantageous configuration for relatively large body vessels. The inventors have determined that a crossbar having a length that is equal to approximately 75% of the diameter of the disc-shaped member, when in a resting configuration, to which the crossbar will be attached provides a particularly advantageous configuration for relatively large body vessels.

The crossbars in a multi-stage occlusion device according to a particular embodiment can have the same length, substantially the same length, or different lengths. Furthermore, each length can be a length described above or a different length. For example, as best illustrated in FIG. 20, the first 1120 and second 1220 crossbars in the exemplary multi-stage occlusion device 1000 have the same length, which is equal to approximately 75% of the diameter of the attached disc-shaped member when in a resting configuration. Alternatively, crossbars in a multi-stage occlusion device can have different lengths. Indeed, one crossbar can have a length within the ranges described above while another crossbar has a length that is outside of the described ranges. This structural arrangement may be advantageous when a multi-stage occlusion device according to a particular embodiment is intended to be used at a point of treatment in a body vessel that has an inner diameter that varies along the length along which the multi-stage occlusion device will be implanted. For example, a multi-stage occlusion device having a first crossbar with a length that is within the relative length ranges described above and a second crossbar with a length that is equal to or greater than the resting diameter of the disc-shaped member to which the crossbar will be attached may be particularly well-suited for use at a point of treatment in a body vessel that is adjacent a bifurcation in the body vessel or at or near another area of increased vessel diameter.

The support frames 1112, 1212 in the exemplary multi-stage occlusion device 1000 comprise multiple core wires and multiple coil wires, as described above. Any suitable number of each can be used in a multi-stage occlusion device according to a particular embodiment; a skilled artisan will be able to determine an appropriate combination based on various considerations, including the desired radial force of the multi-stage occlusion device and the desired overall bulk of the device. The exemplary multi-stage occlusion device 1000 includes three core wires: a first crossbar core wire 1130, a second crossbar core wire 1230, and a common core wire 1020 that extends through each of the disc-shaped members 1118, 1218 multiple times, as described below. A first crossbar coil wire 1132 forms the lumen of the first crossbar 1120 and a second crossbar coil wire 1232 forms the lumen of the second crossbar 1220. In the illustrated embodiment, a first disc-shaped member coil wire 1134 forms the lumen of the first disc-shaped member 1118 and a second disc-shaped member coil wire 1234 forms the lumen of the second disc-shaped member 1218. It is noted, though, that a single coil wire could be used to form the lumens of the first 1118 and second 1218 disc-shaped members. Alternatively, multiple coil wires could be used to form the lumens of the first 1118 and second 1218 disc-shaped members. For example, the inventors have determined that forming the each disc-shaped member of two coil members and using a common core wire is considered suitable. Alternative to the inclusion of a common core wire, each disc-shaped member can comprise a core wire that independently passes through the lumen of the disc-shaped member.

The support frames 1112, 1212 are connected to each other for inclusion in the multi-stage occlusion device 1000. The support frames 1112, 1212 can be connected to each other in any suitable manner and using any suitable structure. A skilled artisan will be able to select an appropriate technique and/or structure for connecting two support frames for inclusion in a multi-stage occlusion device according to a particular embodiment based on various considerations, including the nature of the material forming the individual support frames and the desired bulk of the multi-stage occlusion device. As best illustrated in FIG. 21A, the support frames 1112, 1212 of exemplary multi-stage occlusion device are connected to each other by a common core wire 1020 that extends throughout each of the disc-shaped members 1118, 1218. A first portion of the common core wire 1020 extends through the lumen (e.g., passageway) of the first disc-shaped member coil wire 1134 and a second portion of the common core wire 1020 extends through the lumen (e.g., passageway) of the second disc-shaped member coil wire 1234. The common core wire 1020 passes from one of the disc-shaped members 1118, 1218 to the other of the disc-shaped members 1118, 1218 (e.g., between adjacent turns of coil) at first 1022 and second 1024 attachment points. For example, the common core wire 1020 can pass through the lumen of the first disc-shaped member coil wire 1134 and the lumen of the second disc-shaped member coil wire 1234 and from the first support frame 1112 (e.g., first disc-shaped member 1118) to the second support frame 1212 (e.g., second disc-shaped member 1218) to attach the second support frame 1212 to the first support frame 1112.

The common core wire 1020 can pass through each of the disc-shaped members 1118, 1218 any suitable number of times. The inventors have determined that a core wire 1020 passed through each of the disc-shaped members 1118, 1218 multiple times is considered suitable. The inventors have also determined that a core wire 1020 passed through each of the disc-shaped members 1118, 1218 four (4) times provides disc-shaped members 1118, 1218 with suitable properties. The use of common core wire 1020 to connect the support frames 1112, 1212 is considered particularly advantageous at least because it provides a connected structure without adding substantially to the overall profile or radial bulk of the multi-stage occlusion device 1000 because it does not require an additional member that surrounds an outer surface of one or both frames 1112, 1212.

The common core wire 1020 can have any suitable diameter, and skilled artisans will be able to select a suitable diameter for a common core wire according to a particular embodiment based on various considerations, such as the body vessel within which the multi-stage occlusion device is intended to be implanted and the types of fluid the coverings are expected to encounter once implanted. The inventors have determined that it is advantageous to include a common core wire 1020 that has a diameter smaller than the core wires 1130, 1230 of crossbars 1120, 1220 at least because this improves the radial force of the device when in the deployed configuration.

Alternatively, the support frames 1112, 1212 can be connected to each other in any suitable manner and including any suitable structure. For example, an attachment member, such as a suture, crimp or other suitable member, can be placed around adjacent portions of the two support frames 1112, 1212 and secured. The use of such external attachment members are considered suitable for embodiments in which the overall profile and/or radial bulk of the occlusion device is/are not a primary consideration.

As best illustrated in FIGS. 19 and 20, the support frames 1112, 1212 are advantageously connected to each other such that each is a substantial mirror image of the other. Thus, in the deployed configuration, the crossbars 1120, 1220 extend away from the disc-shaped member of the associated support frame 1112, 1212 in opposite directions. This configuration provides a free member that is available for engagement by a device for repositioning and/or retrieval of the occlusion device 1000 from an initial deployment position within the body vessel.

As described above for the single-stage occlusion devices, any suitable material can be used for the coverings in multi-stage occlusion devices and a skilled artisan will be able to select appropriate materials for coverings in a multi-stage occlusion device according to a particular embodiment based on various considerations, such as the body vessel within which the multi-stage occlusion device is intended to be implanted and the types of fluid the coverings are expected to encounter once implanted. Examples materials considered suitable include all materials suitable for inclusion in single-stage occlusion devices, as described above. Specific examples of suitable materials include synthetic materials, natural materials such as small intestine submucosa (SIS), other extracellular matrix (ECM) materials, other biore-modellable materials, and fixed natural tissues, such as fixed bovine pericardium. Also, the coverings and/or the materials used for the coverings can be coated and/or processed as described above. In the multi-stage occlusion device 1000 illustrated in FIGS. 19 and 20, the coverings 1114, 1214 comprise the same material. It is noted, though, that in multi-stage occlusion devices can include coverings that comprise different materials or the same material that has been coated and/or processed differently. For example, it may be advantageous to include one covering that lacks any coating and another covering that includes a coating comprising a bioactive or that has been processed differently than the first covering.

The multi-stage structure provided by inclusion of the first 1100 and second 1200 stages makes the multi-stage occlusion device 1000 particularly well-suited for use in relatively large body vessels at least because the multi-stage structure increases the overall surface area of the occlusion device 1000 that engages the surface of the body vessel wall when deployed, enhancing the anchoring ability of the device 1000. Also, the inclusion of two coverings 1114, 1214 provides two levels for occlusion of fluid flow, one backing up the other. For example, if there is significant back-flow due to collateral blood flow, the second covering is oriented to occlude that direction. Thus, the multi-stage structure is able to occlude flow from either direction (e.g., antegrade, retrograde) regardless of placement within the body vessel.

FIG. 22 illustrates another exemplary multi-stage occlusion device 2000. The multi-stage occlusion device 2000 is similar to the multi-stage occlusion device 1000 described above and illustrated in FIGS. 19 and 20, except as described below. Thus, the occlusion device 2000 has first 2100 and second 2200 axially adjacent stages. The first stage 2100 includes a first support frame 2112, a first covering 2114, and a first set of one or more attachment members 2116 that attach the first covering 2114 to the first support frame 2112. Similarly, the second stage 2200 includes a second support frame 2212, a second covering 2214, and a second set of one or more attachment members 2216 that attach the second covering 2214 to the second support frame 2212.

The first support frame 2112 comprises a first disc-shaped member 2118 and a first crossbar 2120. The first disc-shaped member 2118 has a first closed circumference 2122 that defines a first central opening 2124. The first crossbar 2120 is connected to the first disc-shaped member 2118 and spans the first central opening 2124. Similarly, the second support frame 2212 comprises a second disc-shaped member 2218 and a second crossbar 2220. The second disc-shaped member 2218 has a second closed circumference 2222 that defines a second central opening 2224. The second crossbar 2220 is connected to the second disc-shaped member 2218 and spans the second central opening 2224.

In the deployed configuration, illustrated in FIG. 22, each of the crossbars 2120, 2220 extends away from the respective disc-shaped member 2118, 2218 to which the crossbar 2120, 2220 is attached. Thus, the crossbars 2120, 2220 extend in opposite directions away from first 2022 and second 2024 attachment points at which the disc-shaped members 2118, 2218 are connected to each other.

Similar to the exemplary multi-stage occlusion device 1000 described above, the first covering 2114 is attached to the first disc-shaped member 2118 by a first set of one or more attachment members 2116 such that the first covering 2114 covers the entire first central opening 2124, effectively closing the first opening 2124. As illustrated in FIG. 22, the first covering 2114 is free, or substantially free, of contact with the first crossbar 2120, excluding only minimal contact that might occur at the attachment points of the first crossbar 2120 to the first disc-shaped member 2118. Thus, the first crossbar 2120 extends over the first covering 2114 from one side of the first disc-shaped member 2118 to an opposite side of the first disc-shaped member 2118. The first covering 2114, therefore, is attached to the first disc-shaped member 2118 such that it lies under, or extends under, the first crossbar 2120.

The second covering 2214 is also attached to the second disc-shaped member 2218 by a second set of one or more attachment members 2216. The second covering 2214 is attached to the second disc-shaped member 2218 in a different manner, however. As illustrated in FIG. 22, the second covering 2214 is attached to the second disc-shaped member 2218 and the second crossbar 2220. This attachment can be made in any suitable manner. As illustrated in FIG. 22, however, it is considered advantageous for the second covering 2214 to be positioned radially outward from the second disc-shaped member 2218 and the second crossbar 2220. In this configuration, the second covering 2214 lies over, or extends over, the second crossbar 2220.

This structural arrangement in which the first covering 2114 lies under the first crossbar 2120 and the second covering extends over the second crossbar 2220 is considered advantageous at least because it leaves the first crossbar 2120 exposed for grasping by a device for repositioning and/or retrieval of the multi-stage occlusion device 2000, while providing additional covering material in the second stage 2200 and associated surface area for contact with fluid within the body vessel intended to be included.

The multi-stage occlusion device 2000 of this embodiment can be placed in a body vessel in any suitable orientation. It is considered advantageous, though, to position the multi-stage occlusion device 2000 in a body vessel such that antegrade flow flows toward the first stage 2100 and then the second stage 2200 (e.g., from left to right in FIG. 22). This orientation allows for retrieval and/or repositioning from an upstream position and orients the second stage, and the "over the crossbar" second covering 2214 as a backup occlusion surface.

FIG. 23 illustrates another exemplary occlusion device 3000. The multi-stage occlusion device 3000 is similar to the multi-stage occlusion device 1000 described above and illustrated in FIGS. 19 and 20, except as described below. Thus, the occlusion device 3000 has first 3100 and second 3200 axially adjacent stages. The first stage 3100 includes a first support frame 3112, a first covering 3114, and a first set of one or more attachment members 3116 that attach the first covering 3114 to the first support frame 3112. Similarly, the second stage 3200 includes a second support frame 3212, a second covering 3214, and a second set of one or more attachment members 3216 that attach the second covering 3214 to the second support frame 3212.

The first support frame 3112 comprises a first disc-shaped member 3118 and a first crossbar 3120a. The first disc-shaped member 3118 has a first closed circumference 3122 that defines a first central opening 3124. The first crossbar 3120a is connected to the first disc-shaped member 3118 and spans the first central opening 3124. In this embodiment, the first support frame 3112 includes a second crossbar 3120b that is also connected to the first disc-shaped member 3118 and spans the first central opening 3124. When the multi-stage occlusion device 3000 is in the deployed configuration, as illustrated in FIG. 23, the first 3120a and second 3120b crossbars extend away from the first disc-shaped member 3118 in opposite directions. The crossbars 3120a, 3120b are oriented on substantially orthogonal planes with respect to a lengthwise axis of the multi-stage occlusion device 3000, but any suitable orientation can be used. Similarly, the second support frame 3212 comprises a second disc-shaped member 3218 and a third crossbar 3220a. The second disc-shaped member 3218 has a second closed circumference 3222 that defines a second central opening 3224. The third crossbar 3220a is connected to the second disc-shaped member 3218 and spans the second central opening 3224. The second support frame 3212 includes a fourth crossbar 3220b that is also connected to the second disc-shaped member 3218 and spans the second central opening 3224. When the multi-stage occlusion device 3000 is in the deployed configuration, as illustrated in FIG. 23, the third 3220a and fourth 3220b crossbars extend away from the second disc-shaped member 3218 in opposite directions. The crossbars 3220a, 3220b are oriented on substantially orthogonal planes with respect to a lengthwise axis of the multi-stage occlusion device 3000, but any suitable orientation can be used.

In this embodiment, first 3100 and second 3200 stages are connected to each other by an attachment 3030 formed between the second crossbar 3120b of the first support frame 3112 and the fourth crossbar 3220b of the second support frame 3212. The support frames 3112, 3212 can be connected to each other in any suitable manner and using any suitable structure. A skilled artisan will be able to select an appropriate technique and/or structure for connecting two support frames for inclusion in a multi-stage occlusion device according to a particular embodiment based on various considerations, including the nature of the material forming the individual support frames and the desired bulk of the multi-stage occlusion device. Examples of suitable attachments include a common core wire extending through each of the second crossbar 3120b of the first support frame 3112 and the fourth crossbar 3220b of the second support frame 3212, and a separately attached member, such as a suture, clip, or other suitable structure.

In this embodiment, the coverings 3114, 3214 can be attached to the disc-shaped support frames 3112, 3212 in any suitable manner, including both "under the crossbar" and "over the crossbar" orientations. In the illustrated embodiment, the first covering 3114 is attached to the first support frame 3112 such that it lies under the first crossbar 3120a of the first support frame 3112 while the second covering 3214 is attached to the second support frame 3212 such that it lies under the third crossbar 3220a of the second support frame 3212. It is noted, though, that any combination of these attachment approaches can be used in a multi-stage orientation device according to a particular embodiment.

This structural arrangement of the components is considered advantageous at least because it allows for a single attachment point between the first 3100 and second 3200 stages. Also, the inclusion of two coverings 3114, 3214 provides two levels for occlusion of fluid flow, one backing up the other. For example, if there is significant back-flow due to collateral blood flow, the second covering is oriented to occlude that direction. Thus, the multi-stage structure is able to occlude flow from either direction (e.g., antegrade, retrograde) regardless of placement within the body vessel.

Example 1

In Vivo Implantation of Occlusion Devices

Nine (9) occlusion devices were implanted in various arterial vessels of sheep (target arteries included carotid, renal, femoral muscular branch, deep femoral, iliac, and pulmonary arteries; vessel diameters ranged from 3 mm to 9 mm). Prior to implantation, each animal was fully heparinized (100 IU heparin/kg body weight). Each of the occlusion devices was constructed to be similar to the embodiment illustrated in FIG. 15.

Sizing Scheme 6 mm devices (outer diameter of the disc-shaped member) were used for vessels with an inner diameter of between about 2.4 and about 3.6 mm.

8 mm devices were used for vessels with an inner diameter of between about 3.6 and about 4.8 mm.

10 mm devices were used for vessels with an inner diameter of between about 4.8 and about 6.0 mm.

12 mm devices were used for vessels with an inner diameter of between about 6.0 and about 7.2 mm.

14 mm devices were used for vessels with an inner diameter of between about 7.2 and about 8.4 mm.

Results

Eight out of nine (8/9) occlusion devices resulted in occlusion, i.e., blocked fluid flow through the vessel at the point of implantation of the occlusion device. The time between implantation and occlusion varied between immediate and about 12 minutes. The ninth occlusion device was retrieved from the animal as described above and was not allowed to remain in the vessel for thrombus formation.

Discussion

Each of the occlusion devices that were allowed to remain in the target vessel for thrombus formation produced occlusion in a relatively short period of time following implantation. Overall, occlusion times were brief despite the heparin treatment given to the animals, and are expected to be even shorter in the absence of such treatment.

Example 2

In Vivo Implantation of Occlusion Devices

Five (5) occlusion devices were implanted in various vessels of an animal (target vessels included distal left deep femoral, proximal left deep femoral, left circumflex, right renal, and right superficial femoral artery (SFA); vessel diameters ranged from about 2.6 mm to about 5.9 mm). Each of the occlusion devices was constructed to be similar to the embodiment illustrated in FIG. 14.

Sizing Scheme 8 mm device was used for implantation into the distal left deep femoral with a vessel diameter of about 3.3 mm.

12 mm device was used for implantation into the proximal left deep femoral with a vessel diameter of about 5.9 mm.

6 mm device was used for implantation into the left circumflex with a vessel diameter of about 2.6 mm.

10 mm device was used for implantation into the right renal with a vessel diameter of about 4.4 mm.

12 mm device was used for implantation into the right SFA with a vessel diameter of about 5.9 mm.

Results

Each of the occlusion devices resulted in acute occlusion without acute migration, i.e., blocked fluid flow through the vessel at the point of implantation of the occlusion device. The time between implantation and occlusion varied between about 2 minutes and about 7 minutes, with an acute occlusion average time of about 4.1 minutes. After one month, four out of five (4/5) occlusion devices resulted in chronic occlusion of the vessel. The occlusion device implanted in the proximal left deep femoral did not result in chronic occlusion.

Discussion

Each of the occlusion devices produced occlusion in a relatively short period of time following implantation and no acute migration of the devices was observed.

Example 3

In Vivo Implantation of Occlusion Devices

Five (5) occlusion devices were implanted in various vessels of an animal (target vessels included left deep femoral, left deep femoral lateral branch, left circumflex, right renal, and right superficial femoral artery (SFA); vessel diameters ranged from about 3.0 mm to about 6.3 mm). Each of the occlusion devices was constructed to be similar to the embodiment illustrated in FIG. 15.

Sizing Scheme 10 mm device was used for implantation into the left deep femoral with a vessel diameter of about 4.4 mm.

8 mm device was used for implantation into the left deep femoral lateral branch with a vessel diameter of about 3.3 mm.

6 mm device was used for implantation into the left circumflex with a vessel diameter of about 3.0 mm.

8 mm device was used for implantation into the right renal with a vessel diameter of about 3.6 mm.

12 mm device was used for implantation into right SFA with a vessel diameter of about 6.3 mm.

Results

Each of the occlusion devices resulted in acute occlusion without acute migration, i.e., blocked fluid flow through the vessel at the point of implantation of the occlusion device. The time between implantation and occlusion varied between about 1 minute and about 10 minutes, with an acute occlusion average time of about 5.5 minutes. After one month, four out of five (4/5) occlusion devices resulted in chronic occlusion of the vessel. The occlusion device implanted in the left deep femoral lateral branch did not result in chronic occlusion.

Discussion

Each of the occlusion devices produced occlusion in a relatively short period of time following implantation and no acute migration of the devices was observed.

The foregoing detailed description refers to exemplary occlusion devices and includes the best mode for practicing the invention. The description and the appended drawings illustrating the described devices are intended only to provide examples and not to limit the scope of the claims in any manner.

What is claimed is:

1. An occlusion device comprising:
a first support frame comprising a first disc-shaped member and a first crossbar, the first disc-shaped member having an outer edge and defining a closed circumference with a central opening, the first disc-shaped member including a first coil defining a first passageway and a first core wire extending through the first passageway, the first crossbar attached to the first disc-shaped member and extending across the central opening and including a second coil defining a second passageway and a second core wire extending through the second passageway;
a first covering attached to the first disc-shaped member and extending across the central opening of the first disc-shaped member;
a second support frame attached to the first support frame and comprising a second disc-shaped member and a second crossbar, the second disc-shaped member having an outer edge and defining a closed circumference with a central opening, the second disc-shaped member including a third coil defining a third passageway and a third core wire extending through the third passageway, the second crossbar attached to the second disc-shaped member and extending across the central opening and including a fourth coil defining a fourth passageway and a fourth core wire extending through the fourth passageway; and
a second covering attached to the second disc-shaped member and extending across the central opening of the second disc-shaped member;
wherein the first core wire comprises a first portion of a common core wire;

wherein the third core wire comprises a second portion of the common core wire;
wherein the common core wire passes through the first passageway and the third passageway and from the first support frame to the second support frame to attach the second support frame to the first support frame;
wherein the first coil comprises a first outer diameter, the second coil comprises a second outer diameter, the third coil comprises a third outer diameter, and the fourth coil comprises a fourth outer diameter;
wherein the second outer diameter is greater than the first outer diameter; and
wherein the fourth outer diameter is greater than the third outer diameter.

2. The occlusion device of claim 1, wherein the common core wire comprises a first diameter;
wherein the second core wire comprises a second diameter;
wherein the fourth core wire comprises a third diameter; and
wherein the first diameter is less than the second diameter and the third diameter.

3. An occlusion device comprising:
a first support frame comprising a first disc-shaped member and a first crossbar, the first disc-shaped member having an outer edge and defining a closed circumference with a central opening, the first disc-shaped member including a first coil defining a first passageway and a first core wire extending through the first passageway, the first crossbar attached to the first disc-shaped member and extending across the central opening and including a second coil defining a second passageway and a second core wire extending through the second passageway;
a first covering attached to the first disc-shaped member and extending across the central opening of the first disc-shaped member;
a second support frame attached to the first support frame and comprising a second disc-shaped member and a second crossbar, the second disc-shaped member having an outer edge and defining a closed circumference with a central opening, the second disc-shaped member including a third coil defining a third passageway and a third core wire extending through the third passageway, the second crossbar attached to the second disc-shaped member and extending across the central opening and including a fourth coil defining a fourth passageway and a fourth core wire extending through the fourth passageway; and
a second covering attached to the second disc-shaped member and extending across the central opening of the second disc-shaped member;
wherein the first disc-shaped member comprises a first diameter;
wherein the second disc-shaped member comprises a second diameter;
wherein the first crossbar comprises a first length that is less than the first diameter; and
wherein the second crossbar comprises a second length that is less than the second diameter.

4. An occlusion device, comprising:
a first support frame comprising a first disc-shaped member and a first crossbar, the first disc-shaped member having an outer edge and defining a closed circumference with a central opening, the first disc-shaped member including a first coil defining a first passageway and a first portion of a common core wire extending through the first passageway, the first crossbar attached to the first disc-shaped member and extending across the central opening and including a second coil defining a second passageway and a first core wire extending through the second passageway;
a first covering attached to the first disc-shaped member and extending across the central opening of the first disc-shaped member;
a second support frame attached to the first support frame and comprising a second disc-shaped member and a second crossbar, the second disc-shaped member having an outer edge and defining a closed circumference with a central opening, the second disc-shaped member including a third coil defining a third passageway and a second portion of the common core wire extending through the third passageway, the second crossbar attached to the second disc-shaped member and extending across the central opening and including a fourth coil defining a fourth passageway and a second core wire extending through the fourth passageway; and
a second covering attached to the second disc-shaped member and extending across the central opening of the second disc-shaped member;
wherein the common core wire passes from the first support frame to the second support frame to attach the second support frame to the first support frame;
wherein the first crossbar extends away from the first disc-shaped member of the first support frame in a first direction and away from the second crossbar; and
wherein the second crossbar extends away from the second disc-shaped member of the second support frame in a second direction different from the first direction and away from the first crossbar.

5. The occlusion device of claim 4, wherein the common core wire passes through the first passageway and the third passageway multiple times.

6. The occlusion device of claim 4, wherein the first crossbar comprises a first length;
wherein the second crossbar comprises a second length; and
wherein the first length is different than the second length.

7. The occlusion device of claim 4, wherein the first covering extends under the first crossbar and is free of attachment to the first crossbar; and
wherein the second covering extends under the second crossbar and is free of attachment to the second crossbar.

8. The occlusion device of claim 4, wherein the first covering extends under the first crossbar and is free of attachment to the first crossbar; and
wherein the second covering extends over the second crossbar and is attached to the second crossbar.

9. An occlusion device, comprising:
a first support frame comprising a first disc-shaped member and a first crossbar, the first disc-shaped member having an outer edge and defining a closed circumference with a central opening, the first disc-shaped member including a first coil defining a first passageway and a first portion of a common core wire extending through the first passageway, the first crossbar attached to the first disc-shaped member and extending across the central opening and including a second coil defining a second passageway and a first core wire extending through the second passageway;
a first covering attached to the first disc-shaped member and extending across the central opening of the first disc-shaped member;
a second support frame attached to the first support frame and comprising a second disc-shaped member and a second crossbar, the second disc-shaped member having an outer edge and defining a closed circumference with a central opening, the second disc-shaped member including a third coil defining a third passageway and a second portion of the common core wire extending through the third passageway, the second crossbar attached to the second disc-shaped member and extending across the central opening and including a fourth coil defining a fourth passageway and a second core wire extending through the fourth passageway; and a second covering attached to the second disc-shaped member and extending across the central opening of the second disc-shaped member;

wherein the common core wire passes from the first support frame to the second support frame to attach the second support frame to the first support frame;

wherein the common core wire passes through the first passageway and the third passageway multiple times;

wherein the first coil comprises a first outer diameter, the second coil comprises a second outer diameter, the third coil comprises a third outer diameter, and the fourth coil comprises a fourth outer diameter; and wherein the second outer diameter is greater than the first outer diameter; and wherein the fourth outer diameter is greater than the third outer diameter.

10. The occlusion device of claim 9, wherein the common core wire comprises a first diameter;

wherein the first core wire comprises a second diameter;

wherein the second core wire comprises a third diameter; and wherein the first diameter is less than the second diameter and the third diameter.

11. An occlusion device, comprising:

a first support frame comprising a first disc-shaped member and a first crossbar, the first disc-shaped member having an outer edge and defining a closed circumference with a central opening, the first disc-shaped member including a first coil defining a first passageway and a first portion of a common core wire extending through the first passageway, the first crossbar attached to the first disc-shaped member and extending across the central opening and including a second coil defining a second passageway and a first core wire extending through the second passageway;

a first covering attached to the first disc-shaped member and extending across the central opening of the first disc-shaped member;

a second support frame attached to the first support frame and comprising a second disc-shaped member and a second crossbar, the second disc-shaped member having an outer edge and defining a closed circumference with a central opening, the second disc-shaped member including a third coil defining a third passageway and a second portion of the common core wire extending through the third passageway, the second crossbar attached to the second disc-shaped member and extending across the central opening and including a fourth coil defining a fourth passageway and a second core wire extending through the fourth passageway; and a second covering attached to the second disc-shaped member and extending across the central opening of the second disc-shaped member;

wherein the common core wire passes from the first support frame to the second support frame to attach the second support frame to the first support frame;

wherein the first disc-shaped member comprises a first diameter;

wherein the second disc-shaped member comprises a second diameter;

wherein the first crossbar comprises a first length that is less than the first diameter; and wherein the second crossbar comprises a second length that is less than the second diameter.

12. An occlusion device, comprising:

a first support frame comprising a first disc-shaped member and a first crossbar, the first disc-shaped member having an outer edge and defining a closed circumference with a central opening, the first disc-shaped member including a first coil defining a first passageway and a first portion of a common core wire extending through the first passageway, the first crossbar attached to the first disc-shaped member and extending across the central opening and including a second coil defining a second passageway and a first core wire extending through the second passageway;

a first covering attached to the first disc-shaped member and extending across the central opening of the first disc-shaped member;

a second support frame attached to the first support frame and comprising a second disc-shaped member and a second crossbar, the second disc-shaped member having an outer edge and defining a closed circumference with a central opening, the second disc-shaped member including a third coil defining a third passageway and a second portion of the common core wire extending through the third passageway, the second crossbar attached to the second disc-shaped member and extending across the central opening and including a fourth coil defining a fourth passageway and a second core wire extending through the fourth passageway; and a second covering attached to the second disc-shaped member and extending across the central opening of the second disc-shaped member;

wherein the common core wire passes from the first support frame to the second support frame to attach the second support frame to the first support frame;

wherein the first crossbar extends away from the first disc-shaped member of the first support frame in a first direction and away from the second crossbar;

wherein the second crossbar extends away from the second disc-shaped member of the second support frame in a second direction different from the first direction and away from the first crossbar; and wherein the common core wire passes through the first passageway and the third passageway multiple times.

13. The occlusion device of claim 12, wherein the first covering extends under the first crossbar and is free of attachment to the first crossbar; and wherein the second covering extends over the second crossbar and is attached to the second crossbar.

* * * * *